(12) United States Patent
McClain et al.

(10) Patent No.: US 9,636,309 B2
(45) Date of Patent: May 2, 2017

(54) MACROLIDE DOSAGE FORMS

(75) Inventors: James B. McClain, Raleigh, NC (US); Charles Douglas Taylor, Franklinton, NC (US); Wenda C. Carlyle, Prairie Farm, WI (US)

(73) Assignee: Micell Technologies, Inc., Durham, NC (US)

( * ) Notice: Subject to any disclaimer, the term of this patent is extended or adjusted under 35 U.S.C. 154(b) by 0 days.

(21) Appl. No.: 13/229,473

(22) Filed: Sep. 9, 2011

(65) Prior Publication Data
US 2012/0064124 A1 Mar. 15, 2012

Related U.S. Application Data

(60) Provisional application No. 61/381,371, filed on Sep. 9, 2010.

(51) Int. Cl.
*A61K 47/34* (2006.01)
*A61K 9/70* (2006.01)
*A61K 9/00* (2006.01)

(52) U.S. Cl.
CPC .......... *A61K 9/7007* (2013.01); *A61K 9/0019* (2013.01); *A61K 9/0021* (2013.01); *A61K 47/34* (2013.01)

(58) Field of Classification Search
CPC .... A61K 47/34; A61K 9/0019; A61K 9/0021; A61K 9/7007
See application file for complete search history.

(56) References Cited

U.S. PATENT DOCUMENTS

| | | | |
|---|---|---|---|
| 3,087,860 | A | 4/1963 | Endicott |
| 4,931,037 | A * | 6/1990 | Wetterman ..................... 604/8 |
| 5,342,621 | A | 8/1994 | Eury |
| 5,470,603 | A | 11/1995 | Staniforth et al. |
| 5,873,904 | A | 2/1999 | Ragheb et al. |
| 5,948,020 | A | 9/1999 | Yoon et al. |
| 5,957,975 | A | 9/1999 | Lafont et al. |
| 6,143,314 | A | 11/2000 | Chandrashekar et al. |
| 6,153,252 | A | 11/2000 | Hossainy et al. |
| 6,273,913 | B1 | 8/2001 | Wright et al. |
| 6,319,541 | B1 | 11/2001 | Pletcher et al. |
| 6,368,658 | B1 | 4/2002 | Schwarz et al. |
| 6,372,246 | B1 | 4/2002 | Wei et al. |
| 6,461,644 | B1 | 10/2002 | Jackson et al. |
| 6,517,860 | B1 | 2/2003 | Roser et al. |
| 6,537,310 | B1 | 3/2003 | Palmaz et al. |
| 6,669,785 | B2 | 12/2003 | DeYoung et al. |
| 6,706,283 | B1 | 3/2004 | Appel et al. |
| 6,736,996 | B1 | 5/2004 | Carbonell |
| 6,749,902 | B2 | 6/2004 | Yonker et al. |
| 6,756,084 | B2 | 6/2004 | Fulton et al. |
| 6,800,663 | B2 | 10/2004 | Asgarzadeh et al. |
| 6,815,218 | B1 | 11/2004 | Jacobson et al. |
| 6,908,624 | B2 | 6/2005 | Hossainy et al. |
| 7,056,591 | B1 | 6/2006 | Pacetti et al. |
| 7,094,256 | B1 | 8/2006 | Shah et al. |
| 7,455,688 | B2 | 11/2008 | Furst et al. |
| 7,611,728 | B2 * | 11/2009 | Kidane ................ A61K 9/0004 424/465 |
| 7,763,277 | B1 | 7/2010 | Canham et al. |
| 7,837,726 | B2 | 11/2010 | Von Oepen et al. |
| 2001/0026804 | A1 | 10/2001 | Boutignon |
| 2001/0049551 | A1 | 12/2001 | Tseng et al. |
| 2003/0088307 | A1 | 5/2003 | Shulze et al. |
| 2003/0157171 | A1 * | 8/2003 | Chornet et al. ............... 424/468 |
| 2003/0170305 | A1 | 9/2003 | O'Neil et al. |
| 2003/0222017 | A1 | 12/2003 | Fulton et al. |
| 2004/0018228 | A1 | 1/2004 | Fischell et al. |
| 2004/0022853 | A1 | 2/2004 | Ashton et al. |
| 2004/0122205 | A1 | 6/2004 | Nathan |
| 2004/0170685 | A1 | 9/2004 | Carpenter et al. |
| 2004/0224001 | A1 | 11/2004 | Pacetti et al. |
| 2004/0236416 | A1 | 11/2004 | Falotico |
| 2005/0010275 | A1 | 1/2005 | Sahatjian et al. |
| 2005/0079199 | A1 | 4/2005 | Heruth et al. |
| 2005/0084533 | A1 | 4/2005 | Howdle et al. |
| 2005/0208102 | A1 | 9/2005 | Schultz |
| 2006/0093771 | A1 | 5/2006 | Rypacek et al. |
| 2006/0094744 | A1 | 5/2006 | Maryanoff et al. |
| 2006/0121080 | A1 | 6/2006 | Lye et al. |
| 2006/0228453 | A1 | 10/2006 | Cromack et al. |
| 2006/0276877 | A1 * | 12/2006 | Owens et al. ............... 623/1.15 |
| 2007/0009564 | A1 | 1/2007 | McClain et al. |

(Continued)

FOREIGN PATENT DOCUMENTS

WO  WO-2005/063319  7/2005
WO  WO 2006/014534  2/2006

(Continued)

OTHER PUBLICATIONS

Muller (Inorganic Structural Chemistry. 1993; John Wiley and Sons:pp. 14-15).*
Substratum [online] retrieved on Feb. 26, 2016 from:http://www.collinsdictionary.com/dictionary/english/substratum#substratum_1; 2 pages.*
Substrate [online] retrieved on Feb. 26, 2016 from: http://www.collinsdictionary.com/dictionary/english/substrate; 3 pages.*
Rey (Freeze-Drying/Lyophilization of Pharmaceutical and Biological Products 2010; 3rd Ed. CRC Press:p. 269).*
PCT/US2011/032371, International Search Report dated Jul. 7, 2011.
Plas, et al., "Tubers and tumors: rapamycin therapy for benign and malignant tumors", Curr Opin Cell Bio 21: 230-236, (2009).
PCT/US2011/051092 International Search Report and Written Opinion on Patentability dated Mar. 27, 2012.
PCT/US2011/051092 International Preliminary Report on Patentability dated Mar. 21, 2013.
Cohen, et al. "Sintering Technique for the Preparation of Polymer Matrices for the Controlled Release of Macromolecules." Journal of Pharamceutical Sciences, vol. 73, No. 8, 1984, p. 1034-1037.

(Continued)

*Primary Examiner* — Ernst V Arnold
(74) *Attorney, Agent, or Firm* — Lerner, David, Littenberg, Krumholz & Mentlik, LLP

(57) ABSTRACT

Provided is a drug delivery composition comprising at least one polymer and at least one active agent; wherein the active agent is present in crystalline form on at least one region of an outer surface of the composition and wherein active agent surface content is adjusted to provide a selected active agent release profile.

11 Claims, No Drawings

(56) References Cited

U.S. PATENT DOCUMENTS

| | | |
|---|---|---|
| 2007/0123977 A1 | 5/2007 | Cottone et al. |
| 2007/0154554 A1 | 7/2007 | Burgermeister et al. |
| 2007/0198081 A1 | 8/2007 | Castro et al. |
| 2007/0280992 A1 | 12/2007 | Margaron |
| 2008/0124372 A1 | 5/2008 | Hossainy et al. |
| 2008/0255510 A1 | 10/2008 | Wang |
| 2009/0043379 A1 | 2/2009 | Prescott |
| 2009/0062909 A1 | 3/2009 | Taylor et al. |
| 2009/0110711 A1 | 4/2009 | Trollsas et al. |
| 2009/0111787 A1 | 4/2009 | Lim et al. |
| 2009/0123515 A1 | 5/2009 | Taylor et al. |
| 2009/0186069 A1 | 7/2009 | DeYoung et al. |
| 2009/0263460 A1 | 10/2009 | McDonald |
| 2009/0292351 A1 | 11/2009 | McClain et al. |
| 2010/0063580 A1 | 3/2010 | McClain et al. |
| 2010/0211164 A1 | 8/2010 | McClain et al. |
| 2010/0239635 A1 | 9/2010 | McClain et al. |
| 2010/0256748 A1 | 10/2010 | Taylor et al. |
| 2010/0272778 A1 | 10/2010 | McClain et al. |
| 2011/0034422 A1 | 2/2011 | Kannan |
| 2011/0257732 A1 | 10/2011 | McClain et al. |
| 2012/0064124 A1 | 3/2012 | McClain et al. |
| 2012/0064143 A1 | 3/2012 | Sharp et al. |
| 2012/0323311 A1 | 12/2012 | McClain et al. |
| 2013/0006351 A1 | 1/2013 | Taylor et al. |

FOREIGN PATENT DOCUMENTS

| | | |
|---|---|---|
| WO | WO 2007/002238 | 1/2007 |
| WO | WO-2007/011707 | 1/2007 |
| WO | WO 2007/011708 | 1/2007 |
| WO | WO-2007/127363 | 11/2007 |
| WO | WO 2008-086369 | 7/2008 |
| WO | WO-2008/086369 | 7/2008 |
| WO | WO-2008/131131 | 10/2008 |
| WO | WO 2008/148013 | 12/2008 |
| WO | WO-2009/146209 | 12/2009 |
| WO | WO 2010/009335 | 1/2010 |
| WO | WO 2010/120552 | 10/2010 |
| WO | WO 2010/121187 | 10/2010 |
| WO | WO 2011/130448 | 10/2011 |
| WO | WO 2012/142319 | 10/2012 |

OTHER PUBLICATIONS

Jovanovic et al. "Stabilization of Proteins in Dry Powder Formulations Using Supercritical Fluid Technology," Pharm. Res. 2004; 21(11).
Merriam-Webster Online Dictionary, obtained online at: http://www.merriam-webster.com/dictionary/derivative, downloaded Jan. 23, 2013.
Mishima et al. "Microencapsulation of Proteins by Rapid Expansion of Supercritical Solution with a Nonsolvent," AIChE J. 2000;46(4):857-65.
PCT/US06/24221 International Preliminary Report on Patentability dated Dec. 24, 2007.
PCT/US06/24221 International Search Report mailed Jan. 29, 2007.
PCT/US06/27321 International Preliminary Report on Patentability dated Jan. 16, 2008.
PCT/US06/27321 International Search Report mailed Oct. 16, 2007.
PCT/US06/27322 International Preliminary Report on Patentability dated Jan. 16, 2008.
PCT/US06/27322 International Search Report mailed Apr. 25, 2007.
PCT/US07/10227 International Preliminary Report on Patentability dated Oct. 28, 2008.
PCT/US07/10227 International Search Report mailed Aug. 8, 2008.
PCT/US08/50536 International Preliminary Report on Patentability dated Jul. 14, 2009.
PCT/US08/50536 International Search Report mailed Jun. 2, 2008.
PCT/US08/60671 International Preliminary Report on Patentability dated Oct. 20, 2009.
PCT/US08/60671 International Search Report mailed Sep. 5, 2008.
PCT/US09/41045 International Preliminary Report on Patentability dated Oct. 19, 2010.
PCT/US09/41045 International Search Report mailed Aug. 11, 2009.
PCT/US10/29494 International Preliminary Report on Patentability dated Oct. 4, 2011.
PCT/US10/29494 Search Report and Written Opinion mailed Feb. 7, 2011.
PCT/US10/31470 International Preliminary Report on Patentability dated Oct. 18, 2011.
PCT/US10/31470 Search Report and Written Opinion mailed Jan. 28, 2011.
PCT/US11/032371 International Report on Patentability dated Oct. 16, 2012.
PCT/US11/032371 International Search Report mailed Jul. 7, 2011.
PCT/US12/33367 International Preliminary Report on Patentability dated Oct. 15, 2013.
PCT/US12/33367 International Search Report mailed Aug. 1, 2012.
Sahajanand Medical Technologies (Supralimus Core; Jul. 6, 2008).
Scheuffler et al., "Crystal Structure of Human Bone Morphogenetic Protein-2 at 2.7 Angstrom resolution," Journal of Molecular Biology, vol. 287, Issue 1, Mar. 1999, retrieved online at http://www.sciencedirect.com/science/article/pii/S0022283699925901.
Serruys, Patrick et al., Comparison of Coronary-Artery Bypass Surgery and Stenting for the Treatment of Multivessel Disease, N. Engl. J. Med., 2001, vol. 344, No. 15, pp. 1117-1124.
Shekunov et al. "Crystallization Processes in Pharmaceutical Technology and Drug Delivery Design." Journal of Crystal Growth 211 (2000), pp. 122-136.
U.S. Appl. No. 11/158,724 Office Action Mailed Sep. 26, 2012.
U.S. Appl. No. 11/158,724 Office Action Mailed Sep. 8, 2008.
U.S. Appl. No. 11/995,685 Office Action Mailed Aug. 20, 2010.
U.S. Appl. No. 11/995,685 Office Action Mailed Nov. 24, 2009.
U.S. Appl. No. 11/995,687 Office Action Mailed Sep. 28, 2011.
U.S. Appl. No. 12/298,459 Office Action Mailed Apr. 6, 2012.
U.S. Appl. No. 12/298,459 Office Action Mailed Aug. 10, 2011.
U.S. Appl. No. 12/298,459 Office Action Mailed May 31, 2013.
U.S. Appl. No. 11/158,724 Office action Mailed May 23, 2013.
U.S. Appl. No. 11/158,724 Office Action Mailed Sep. 17, 2009.
U.S. Appl. No. 12/426,198 Office Action Mailed Feb. 6, 2012.
U.S. Appl. No. 12/426,198 Office Action Mailed Mar. 23, 2011.
U.S. Appl. No. 12/522,379 Final Office Action Mailed Aug. 28, 2013.
U.S. Appl. No. 12/522,379 Office Action Mailed Dec. 26, 2012.
U.S. Appl. No. 12/595,848 Office Action Mailed Jan. 13, 2012.
U.S. Appl. No. 12/595,848 Office Action Mailed Mar. 15, 2013.
U.S. Appl. No. 12/595,848 Office Action Mailed Oct. 22, 2013.
U.S. Appl. No. 12/751,902 Office Action Mailed Jul. 13, 2012.
U.S. Appl. No. 12/762,007 Final Office action Mailed Oct. 22, 2013.
U.S. Appl. No. 12/762,007 Office action Mailed Feb. 11, 2013.
U.S. Appl. No. 13/086,335 Office action Mailed May 22, 2013.
U.S. Appl. No. 13/605,904 Office Action Mailed Jun. 28, 2013.
U.S. Appl. No. 13/605,904 Office Action Mailed Nov. 27, 2012.
PCT/US2013/041466 International Search Report and Written Opinion dated Oct. 17, 2013.
PCT/US2013/041466 International Preliminary Report on Patentability dated Nov. 18, 2014.
U.S. Appl. No. 11/158,724 Office Action Mailed Dec. 31, 2013.
U.S. Appl. No. 11/158,724 Office Action Mailed Jun. 25, 2014.

\* cited by examiner

MACROLIDE DOSAGE FORMS

CROSS-REFERENCE

This application claims priority to U.S. Provisional Application No. 61/381,371 filed Sep. 9, 2010. The entire content of this application is incorporated herein by reference.

BACKGROUND OF THE INVENTION

Oral administration of rapamycin suffers from poor bioavailability and once-daily dosing results in fluctuating peak and trough blood levels. Immunosuppressive effectiveness of rapamycin and other limus compounds is dose dependent requiring that trough levels of drug remain in the therapeutic range. Too high blood levels of drug are linked to adverse and overtly toxic effects. It is desirable to maintain blood levels of drug within a therapeutic window.

SUMMARY OF THE INVENTION

One embodiment provides a drug delivery composition comprising at least one polymer and at least one active agent; wherein the active agent is present in crystalline form on at least one region of an outer surface of the composition and wherein active agent surface content is adjusted to provide a selected active agent release profile.

One embodiment provides a drug delivery composition wherein presence of active agent on at least a region of the surface of the composition is determined by cluster secondary ion mass spectrometry (cluster SIMS).

One embodiment provides a drug delivery composition wherein presence of active agent on at least a region of the surface of the composition is determined by generating cluster secondary ion mass spectrometry (cluster SIMS) depth profiles.

One embodiment provides a drug delivery composition wherein presence of active agent on at least a region of the surface of the composition is determined by time of flight secondary ion mass spectrometry (TOF-SIMS).

One embodiment provides a drug delivery composition wherein presence of active agent on at least a region of the surface of the composition is determined by atomic force microscopy (AFM).

One embodiment provides a drug delivery composition wherein presence of active agent on at least a region of the surface of the composition is determined by X-ray spectroscopy.

One embodiment provides a drug delivery composition of claim 1, wherein presence of active agent on at least a region of the surface of the composition is determined by electron microscopy.

One embodiment provides a drug delivery composition of claim 1, wherein presence of active agent on at least a region of the surface of the composition is determined by Raman spectroscopy.

Provided herein is a drug delivery composition comprising at least one bioabsorbable polymer and at least one active agent; wherein at least a portion of the active agent is in crystalline form; wherein the composition is in a form suitable for administration by injection and comprises polymer and active agent to provide a selected active agent controlled release profile.

One embodiment provides a composition wherein the biologically active agent is encapsulated in microparticles or nanoparticles.

One embodiment provides a composition wherein the bioabsorbable polymer has a glass transition temperature between 45 and 60° C.

One embodiment provides a composition wherein the bioabsorbable polymer gels at body temperature subsequent to heating the composition above the Tg temperature whereby the heated composition can be delivered in the form of bleb (flowable composition).

One embodiment provides a composition wherein the active agent is selected from rapamycin, a prodrug, a derivative, an analog, a hydrate, an ester, and a salt thereof.

One embodiment provides a composition wherein the active agent is selected from one or more of sirolimus, everolimus, zotarolimus and biolimus.

One embodiment provides a composition wherein the active agent comprises a macrolide immunosuppressive (limus) drug.

One embodiment provides a composition wherein the macrolide immunosuppressive drug comprises one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycarbonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, polymorphs, isomers, racemates, diastereoisomers, prodrugs, hydrate, ester, or analogs thereof.

One embodiment provides a composition wherein the active agent is at least 50% crystalline.

One embodiment provides a composition wherein the active agent is at least 75% crystalline.

One embodiment provides a composition wherein the active agent is at least 90% crystalline.

One embodiment provides a composition wherein the polymer comprises a PLGA copolymer.

One embodiment provides a composition wherein the composition comprises a first PLGA copolymer with a ratio of about 40:60 to about 60:40 and a second PLGA copolymer with a ratio of about 60:40 to about 90:10.

One embodiment provides a composition wherein the bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly (trimethylcarbonate), p(CPP:SA) poly(1,3-bis-p-(carboxyphenoxy)propane-co-sebacic acid).

One embodiment provides a composition wherein between 25% and 45% of the total amount of active agent in the composition is released after 24 hours in vitro release in a 1:1 spectroscopic grade ethanol/phosphate buffer saline at pH 7.4 and 37° C.; wherein the amount of the active agent released is determined by measuring UV absorption at 278 nm by a diode array spectrometer.

One embodiment provides a composition wherein the composition has mucoadhesive properties.

One embodiment provides a composition wherein the mucoadhesive properties are provided by the bioabsorbable polymer.

One embodiment provides a composition wherein the composition is suitable for injection into a solid tumor to treat the neoplasm.

One embodiment provides a composition wherein the composition is suitable for injection or infusion into the bladder to treat bladder cancer.

One embodiment provides a composition wherein the composition is suitable for injection into vitreous humor of the eye to treat ocular disease.

One embodiment provides a composition wherein the composition is suitable for injection into the prostate gland to treat prostate cancer.

One embodiment provides a composition wherein the composition is suitable for injection into the nasal turbinates to treat chronic sinusitis.

One embodiment provides a composition wherein the composition is suitable for injection into intervention site.

One embodiment provides a composition wherein the intervention site is a wall of a body cavity.

One embodiment provides a composition wherein the body cavity is the result of a lumpectomy.

One embodiment provides a composition wherein the intervention site is a cannulized site within a subject.

One embodiment provides a composition wherein the intervention site is a sinus wall.

One embodiment provides a composition wherein the intervention site is located in the reproductive system of a subject.

One embodiment provides a composition wherein the composition is adapted to treat an ailment of the reproductive system.

One embodiment provides a composition wherein the intervention site is located in the urinary system of a subject.

One embodiment provides a composition wherein the composition is adapted to treat a disease of the urinary system.

One embodiment provides a composition wherein the intervention site is located at a tumor site.

One embodiment provides a composition wherein the tumor site is where a tumor is located.

One embodiment provides a composition wherein the tumor site is where a tumor was located prior to removal and/or shrinkage of the tumor.

One embodiment provides a composition wherein the intervention site is located in the ear.

One embodiment provides a composition wherein the intervention site is located in the esophagus.

One embodiment provides a composition wherein the intervention site is located in the larynx.

One embodiment provides a composition wherein the intervention site is a location of an injury.

One embodiment provides a composition wherein the intervention site is a location of an articulated joint.

One embodiment provides a composition wherein the intervention site is an infection site.

One embodiment provides a composition wherein the infection site is a site wherein an infection may occur, and wherein the active agent is capable of substantially preventing the infection.

One embodiment provides a composition wherein the infection site is a site wherein an infection has occurred, and wherein the active agent is capable of slowing spread of the infection.

One embodiment provides a composition wherein the intervention site is a surgery site.

One embodiment provides a composition wherein the intervention site is an ocular site.

One embodiment provides a composition wherein the composition is capable of at least one of: retarding healing, delaying healing, and preventing healing.

One embodiment provides a composition wherein the composition is capable of at least one of: retarding, delaying, and preventing the inflammatory phase of healing.

One embodiment provides a composition wherein the composition is capable of at least one of: retarding, delaying, and preventing the proliferative phase of healing.

One embodiment provides a composition wherein the active agent and the polymer are in the same layer, in separate layers, or form overlapping layers.

One embodiment provides a composition, wherein the plurality of layers comprise five layers deposited as follows: a first polymer layer, a first active agent layer, a second polymer layer, a second active agent layer and a third polymer layer.

One embodiment provides a composition wherein the plurality of layers comprise five layers deposited as follows: a first polymer layer, a first pharmaceutical agent layer, a second polymer layer, a second pharmaceutical agent layer and a third polymer layer.

One embodiment provides a composition wherein the composition releases the active agent at a selected therapeutic level over a period of at least 48 hours after injection.

One embodiment provides a composition wherein the composition releases the active agent with a linear release profile until about 30% of total content is released. One embodiment provides a composition wherein the composition releases the active agent with a linear release profile until about 50% of total content is released. One embodiment provides a composition wherein the composition releases the active agent with a linear release profile until about 70% of total content is released.

One embodiment provides a composition wherein the composition reduces or eliminates adverse toxic effect associated with oral formulation of the active agent.

One embodiment provides a composition wherein the composition is suitable for intramuscular injection or intraperitoneal injection.

One embodiment provides a composition wherein the composition is suitable for intraarticular, intrathecal, intravesicular or subcutaneous injection.

One embodiment provides a transdermal drug delivery system, comprising: (a) an impervious backing sheet; and (b) a reservoir containing a transdermal drug delivery composition, which comprises at least one bioabsorbable polymer and at least one active agent; wherein at least a portion of the active agent is in crystalline form; wherein the composition is in a form suitable for transdermal administration and comprises polymer and active agent layers formed to provide a selected active agent controlled release profile.

One embodiment provides a transdermal drug delivery system further comprising a microprotrusion member having a plurality of stratum corneum piercing microprotrusions thereon and being adapted for piercing the stratum corneum to improve transdermal flux of the composition.

One embodiment provides a transdermal drug delivery system wherein the reservoir comprises a jet dispenser comprising an orifice, and a container that holds and delivers the composition to said orifice for ejection therethrough.

One embodiment provides a transdermal drug delivery system further comprising a substantially planar substrate having an array of spaced apertures therein; and a plurality of microneedles projecting at angle from the plane in which the planar substrate lies.

One embodiment provides a transdermal drug delivery system wherein the at least one of the microneedles has a substantially rectangular cross-sectional shape in a plane parallel to the substrate.

One embodiment provides a transdermal drug delivery system wherein the at least one channel is open to two opposing surfaces of the microneedle.

One embodiment provides a transdermal drug delivery system wherein the at least one channel terminates in the body portion of the microneedle and does not extend into the tapered tip portion.

One embodiment provides a transdermal drug delivery system wherein the substrate and the microneedles comprise at least one biocompatible metal.

One embodiment provides a transdermal drug delivery system wherein the substrate and the microneedles comprise a stainless steel.

One embodiment provides an oral dosage form comprising a solid support core of a substantially water soluble, swellable or insoluble material and a composition comprising at least one bioabsorbable polymer and at least one active agent; wherein at least a portion of the active agent is in crystalline form; wherein the composition is in a form suitable for oral administration and comprises polymer and active agent layers formed to provide a selected active agent controlled release profile.

One embodiment provides an oral dosage further comprising a release-retarding composition layer.

One embodiment provides an oral dosage wherein the release retarding composition is a polymer having properties suitable for use in enteric coatings.

One embodiment provides an oral dosage further comprising one or more sub-coats beneath the release retarding composition layer.

One embodiment provides an oral dosage further comprising one or more over-coats above the release retarding composition layer.

One embodiment provides an oral dosage wherein the enteric coating further comprises a plasticizer.

One embodiment provides an oral dosage wherein the enteric polymer further comprises an anti-foaming agent.

One embodiment provides an oral dosage wherein the composition is coated with a top coat.

One embodiment provides an oral dosage wherein the top coat is hydroxypropylmethylcellulose.

One embodiment provides an oral dosage wherein the top coat is mucoadhesive.

One embodiment provides a drug delivery composition comprising at least one hydrogel and at least one active agent; wherein the active agent is present in crystalline form and is embedded in the hydrogel.

Another embodiment provides the drug delivery composition wherein the composition indicates the presence of said pharmaceutical agent in crystalline form upon analysis by an analytical method selected from: (a) X-ray spectroscopy, (b) scanning electron microscopy (SEM), (c) Raman spectrum, (d) Differential Scanning calorimetry (DSC), (e) Wide Angle X-ray Scattering (WAXS) spectroscopy, and (f) wide angle radiation scattering spectroscopy.

Another embodiment provides the drug delivery composition wherein curing of the hydrogel occurs in-vivo.

Another embodiment provides the drug delivery composition wherein the composition is formed to provide a selected active agent controlled release profile.

Another embodiment provides the drug delivery composition wherein the composition is in a form suitable for a mode of administration selected from: (a) injection, (b) intramuscular injection, (c) subcutaneous injection, (d) intrathecal injection, (e) intramuscular injection, (f) intraarticular injection, (g) intraperitoneal injection, (h) dermal administration, and (i) during a surgical procedure.

Another embodiment provides the drug delivery composition wherein the composition is adapted for delivery to at least one of: the front of the eye, the back of the eye, the location of a tumor, the location of cancerous cells, the location of cancerous tissue, the former location of cancerous tissue, the former location of cancerous cells, the former location of a tumor, the brain, a neurologic site, a location where inflammation is occurring, a location where inflammation may occur, a location where inflammation is expected to occur.

Another embodiment provides the drug delivery composition wherein the composition is adapted for dural repair.

Another embodiment provides the drug delivery composition wherein the composition is adapted to treat at least one of: intracranial aneurysms, tumors, and spinal disc disease.

Another embodiment provides the drug delivery composition wherein the composition is adapted to stop, slow, or prevent cervical spinal fluid leaks.

Another embodiment provides the drug delivery composition wherein the composition is capable of maintaining a seal under high pressures.

Another embodiment provides the drug delivery composition wherein the composition degrades as natural healing occurs.

Another embodiment provides the drug delivery composition wherein the composition acts as an adhesion barrier.

Another embodiment provides the drug delivery composition wherein the composition acts as a bandage.

Another embodiment provides the drug delivery composition wherein the composition is adapted to cover an opening in the eye and providing a protective barrier to the portion of the eye that is covered.

Another embodiment provides the drug delivery composition wherein the composition comprises voids.

Another embodiment provides the drug delivery composition wherein tissue ingrowth occurs in the voids as tissue heals.

Another embodiment provides the drug delivery composition wherein the composition is in the form of a mesh.

Another embodiment provides the drug delivery composition wherein the composition is adapted to seal tissue.

Another embodiment provides the drug delivery composition wherein the composition may be used in place of or in combination with tacks, staples, sutures, or O-rings in surgical procedures to seal tissue.

Another embodiment provides the drug delivery composition wherein the composition bioabsorbs or degrades as tissue grows into the voids of the mesh and into areas where the hydrogel has been degraded or absorbed.

Another embodiment provides the drug delivery composition wherein the hydrogel is biodegradable.

Another embodiment provides the drug delivery composition wherein the hydrogel is anti-microbial.

Another embodiment provides the drug delivery composition wherein the biologically active agent is encapsulated in microparticles or nanoparticles.

Another embodiment provides the drug delivery composition wherein the composition further comprises one or more agents that modulate the viscosity of the composition.

Another embodiment provides the drug delivery composition wherein the agent that modulates the viscosity of the composition lowers the viscosity of the composition at room temperature.

Another embodiment provides the drug delivery composition wherein the agent that modulates the viscosity of the composition increases the viscosity of the composition at temperatures above 35° C.

Another embodiment provides the drug delivery composition wherein the active agent is selected from rapamycin, a prodrug, a derivative, an analog, a hydrate, an ester, and a salt thereof.

Another embodiment provides the drug delivery composition wherein the active agent is selected from one or more of sirolimus, everolimus, zotarolimus and biolimus.

Another embodiment provides the drug delivery composition wherein the active agent comprises a macrolide immunosuppressive (limus) drug.

Another embodiment provides the drug delivery composition wherein the active agent is a macrolide immunosuppressive drug selected from one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycarbonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, polymorphs, isomers, racemates, diastereoisomers, prodrugs, hydrate, ester, or analogs thereof.

Another embodiment provides the drug delivery composition wherein the active agent is at least 50% crystalline, at least 75% crystalline, or at least 90% crystalline.

Another embodiment provides the drug delivery composition wherein the hydrogel comprises a polymer.

Another embodiment provides the drug delivery composition wherein the polymer comprises a PLGA copolymer.

Another embodiment provides the drug delivery composition wherein the polymer comprises a first PLGA copolymer with a ratio of about 40:60 to about 60:40 and a second PLGA copolymer with a ratio of about 60:40 to about 90:10.

Another embodiment provides the drug delivery composition wherein the polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

Another embodiment provides the drug delivery composition wherein between 25% and 45% of the total amount of active agent in the composition is released after 24 hours in vitro release in a 1:1 spectroscopic grade ethanol/phosphate buffer saline at pH 7.4 and 37° C.; wherein the amount of the active agent released is determined by measuring UV absorption at 278 nm by a diode array spectrometer.

Another embodiment provides the drug delivery composition wherein the composition is suitable for use in a mode of administration selected from: (a) injection into the bladder to treat bladder cancer, (b) injection into the prostate gland to treat prostate cancer, (c) injection into or near the vitreous humor of the eye to treat ocular disease, and (d) injection into the nasal turbinates to treat chronic sinusitis.

Another embodiment provides the drug delivery composition wherein the composition is suitable for injection into an intervention site wherein the intervention site is selected from: (a) the wall of a body cavity, (b) the wall of a body cavity resulting from partial or complete tumor removal, (c) a cannulized site within a subject, (d) a nasal turbinate, (e) within the reproductive system of a subject, (f) within the urinary system of a subject, (g) located at a tumor site, (f) a location in the ear, (g) a location in the esophagus, (h) a location in the larynx, (i) a location of an injury, (j) an infection site, (k) a surgery site, (l) an ocular site, (m) an inflammatory site, or (n) an arthritic joint.

Another embodiment provides the drug delivery composition wherein the composition is adapted to treat an ailment selected from: (a) an ailment of the reproductive system, (b) an ailment of the urinary system.

Another embodiment provides the drug delivery composition wherein the composition is adapted for delivery to at least one of an intervention site, an infection site, and an inflammatory site.

Another embodiment provides the drug delivery composition adapted for delivery to an intervention site wherein the intervention site is located in the urinary system of a subject.

Another embodiment provides the drug delivery composition adapted for delivery to an intervention site wherein the intervention site is located at a tumor site.

Another embodiment provides the drug delivery composition adapted for delivery to a tumor site wherein the tumor site is where a tumor is located.

Another embodiment provides the drug delivery composition adapted for delivery to a tumor site wherein the tumor site is where a tumor was located prior to removal and/or shrinkage of the tumor.

Another embodiment provides the drug delivery composition adapted for delivery to an intervention site wherein the intervention site is located in the ear.

Another embodiment provides the drug delivery composition adapted for delivery to an intervention site wherein the intervention site is located in the esophagus.

Another embodiment provides the drug delivery composition adapted for delivery to an intervention site wherein the intervention site is located in the larynx.

Another embodiment provides the drug delivery composition adapted for delivery to an intervention site wherein the intervention site is a location of an injury.

Another embodiment provides the drug delivery composition adapted for delivery to an intervention site wherein the intervention site is an infection site.

Another embodiment provides the drug delivery composition wherein the composition is adapted for delivery to an inflammatory site wherein the inflammatory site is a site wherein inflammation may occur, and wherein the active agent is capable of substantially preventing the inflammation.

Another embodiment provides the drug delivery composition wherein the composition is adapted for delivery to an inflammatory site wherein the inflammatory site is a site wherein inflammation may occur, and wherein the active agent is capable of substantially reducing the inflammation.

Another embodiment provides the drug delivery composition wherein the composition is adapted for delivery to an infection site wherein the infection site is a site wherein an infection may occur, and wherein the active agent is capable of substantially preventing the infection.

Another embodiment provides the drug delivery composition wherein the composition is adapted for delivery to an infection site wherein the infection site is a site wherein an infection has occurred, and wherein the active agent is capable of slowing spread of the infection.

Another embodiment provides the drug delivery composition wherein the composition is adapted for delivery to an intervention site wherein the intervention site is an ocular site.

Another embodiment provides the drug delivery composition wherein the composition is capable of at least one of: retarding healing, delaying healing, and preventing healing.

Another embodiment provides the drug delivery composition wherein the composition is capable of at least one of: retarding, delaying, and preventing the inflammatory phase of healing.

Another embodiment provides the drug delivery composition wherein the composition is capable of at least one of: retarding, delaying, and preventing the proliferative phase of healing.

Another embodiment provides the drug delivery composition wherein the active agent and the polymer are in the same layer, in separate layers, or form overlapping layers.

Another embodiment provides the drug delivery composition wherein the active agent is uniformly dispersed within the composition.

Another embodiment provides the drug delivery composition wherein the active agent release profile is a linear release profile until 30% of the total content of active agent is released.

Another embodiment provides the drug delivery composition wherein the active agent release profile is a linear release profile until 50% of the total content of active agent is released.

Another embodiment provides the drug delivery composition wherein the composition releases the active agent at a selected therapeutic level over a period of at least 48 hours after injection.

Another embodiment provides the drug delivery composition wherein the composition reduces or eliminates adverse toxic effect associated with oral formulation of the active agent.

Another embodiment provides the drug delivery composition wherein the composition is suitable for intramuscular injection or intraperitoneal injection.

Another embodiment provides the drug delivery composition wherein the active agent is delivered transdermally from the composition at a selected active agent release profile.

Another embodiment provides the transdermal drug delivery composition further comprising a microprotrusion member having a plurality of stratum corneum piercing microprotrusions thereon and being adapted for piercing the stratum corneum to improve transdermal flux of the composition.

Another embodiment provides the transdermal drug delivery composition wherein the composition releases the active agent at a selected therapeutic level over a period of at least 48 hours after application of the composition.

Another embodiment provides the transdermal drug delivery composition wherein the composition reduces or eliminates adverse toxic effect associated with oral formulation of the active agent.

Another embodiment provides the drug delivery composition wherein the composition is adapted for delivery intra-articularly.

Another embodiment provides the drug delivery composition wherein the hydrogel comprises a hydrogel composition that is derived from an activated polyalkylene glycol diacid derivative and a crosslinking agent.

Another embodiment provides the drug delivery composition comprising a hydrogel composition wherein the activated polyalkylene diacid derivative is represented by formula (I):

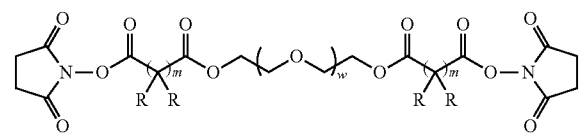

wherein, independently for each occurrence, R is H or lower alkyl; m is 2-20 inclusive; and w is 5 to 1,000 inclusive.

Another embodiment provides the drug delivery composition comprising a hydrogel composition wherein the crosslinking agent is a polyalkyleneimine or trilysine.

Another embodiment provides the drug delivery composition comprising a hydrogel composition wherein the crosslinking agent is polyethyleneimine having a molecular weight of about 2000.

Another embodiment provides the drug delivery composition comprising a hydrogel composition wherein the crosslinking agent is trilysine.

Another embodiment provides the drug delivery composition comprising a hydrogel component of formula (I) wherein m is 2-10 inclusive.

Another embodiment provides the drug delivery composition comprising a hydrogel component of formula (I) wherein m is 2.

Another embodiment provides the drug delivery composition comprising a hydrogel component of formula (I) wherein m is 3.

Another embodiment provides the drug delivery composition comprising a hydrogel component of formula (I) wherein m is 4.

Another embodiment provides the drug delivery composition comprising a hydrogel component of formula (I) wherein m is 6.

Another embodiment provides the drug delivery composition comprising a hydrogel component of formula (I) wherein m is 8.

Another embodiment provides the drug delivery composition comprising a hydrogel component of formula (I) wherein w is 20 to 120 inclusive.

Another embodiment provides the drug delivery composition comprising a hydrogel component of formula (I) wherein w is 120 to 250 inclusive.

Another embodiment provides the drug delivery composition comprising a hydrogel composition wherein the activated polyalkylene glycol diacid derivative is R-PEG$_n$-R; wherein n represents the number average molecular weight of the PEG and is about 2000 to about 12,000 inclusive; and R is SS, SG, SA, SSub, or SSeb.

Another embodiment provides the drug delivery composition comprising a hydrogel composition wherein the activated polyalkylene glycol diacid derivative is PEG$_{3350}$-(SS)$_2$.

Another embodiment provides the drug delivery composition comprising a hydrogel composition wherein the activated polyalkylene glycol diacid derivative is (SS)-PEG$_{3350}$-(SS).

Another embodiment provides the drug delivery composition comprising a hydrogel composition wherein the activated polyalkylene glycol diacid derivative is PEG$_{3350}$-(SG)$_2$.

Another embodiment provides the drug delivery composition comprising a hydrogel composition wherein the activated polyalkylene glycol diacid derivative is (SG)-PEG$_{3350}$-(SG).

Another embodiment provides the drug delivery composition comprising a hydrogel composition wherein the activated polyalkylene glycol diacid derivative is PEG$_{3350}$-(SA)$_2$.

Another embodiment provides the drug delivery composition comprising a hydrogel composition wherein the activated polyalkylene glycol diacid derivative is (SA)-PEG$_{3350}$-(SA).

Another embodiment provides the drug delivery composition comprising a hydrogel composition wherein the activated polyalkylene glycol diacid derivative is PEG$_{3350}$-(SSeb)$_2$.

Another embodiment provides the drug delivery composition comprising a hydrogel composition wherein the activated polyalkylene glycol diacid derivative is (SSeb)-PEG$_{3350}$-(SSeb).

Another embodiment provides the drug delivery composition comprising a hydrogel composition wherein the activated polyalkylene glycol diacid derivative is PEG$_{3350}$-(SSub)$_2$.

Another embodiment provides the drug delivery composition comprising a hydrogel composition wherein the activated polyalkylene glycol diacid derivative is (SSub)-PEG$_{3350}$-(SSub).

Another embodiment provides the drug delivery composition comprising a hydrogel component wherein the weight percent crosslinker is between about 5% and about 50%.

Another embodiment provides the drug delivery composition comprising a hydrogel component wherein the weight percent crosslinker is about 15%.

Another embodiment provides the drug delivery composition comprising a hydrogel component wherein the ratio of activated esters on the polyalkylene glycol diacid derivatives to primary amines on the crosslinking agent is in the range from about 0.10:1 to about 10:1.

Another embodiment provides the drug delivery composition comprising a hydrogel component wherein the ratio of activated esters on the polyalkylene glycol diacid derivatives to primary amines on the crosslinking agent is in the range from about 0.75:1 to about 1.3:1.

Another embodiment provides the drug delivery composition comprising a hydrogel component wherein R is methyl or H.

Another embodiment provides the drug delivery composition comprising a hydrogel component wherein R is H.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof. This application relates to U.S. Provisional Application No. 61/226,239 filed Jul. 16, 2009; U.S. Provisional Application No. 61/081,691, filed Jul. 17, 2008, and U.S. Provisional Application No. 61/212,964, filed Apr. 17, 2009. The contents of these applications are incorporated herein by reference in their entirety.

DEFINITIONS

As used in the present specification, the following words and phrases are generally intended to have the meanings as set forth below, except to the extent that the context in which they are used indicates otherwise.

"Drug delivery composition" as used herein refers to a composition capable of delivering a drug when administered to a subject independently of a substrate such as a stent or other medical device coated with the composition. Once the composition is administered to the subject, the composition is separated from the device used to administer the composition (e.g., a syringe) and drug delivery is carried out by the drug delivery composition without the need for a substrate. It should be noted that embodiments described herein and claimed below when reference is not made to "drug delivery composition" include compositions that are delivered as part of a device such as a transdermal delivery device.

Examples of pharmaceutical agents employed in conjunction with the invention include, rapamycin, 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allylrapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy) ethoxycar-bonylmethyl-rapamycin, 40-O-(3-Hydroxy) propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy) ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), and 42-[3-hydroxy-2-(hydroxymethyl)-2-methylpropanoate]rapamycin (temsirolimus).

The pharmaceutical agents may, if desired, also be used in the form of their pharmaceutically acceptable salts or derivatives (meaning salts which retain the biological effectiveness and properties of the compounds of this invention and which are not biologically or otherwise undesirable), and in the case of chiral active ingredients it is possible to employ both optically active isomers and racemates or mixtures of diastereoisomers. As well, the pharmaceutical agent may include a prodrug, a hydrate, an ester, a polymorph, a derivative or analogs of a compound or molecule.

The pharmaceutical agent may be an antibiotic agent, as described herein.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound.

An "anti-cancer agent", "anti-tumor agent" or "chemotherapeutic agent" refers to any agent useful in the treatment of a neoplastic condition. There are many chemotherapeutic agents available in commercial use, in clinical evaluation and in pre-clinical development that are useful in the devices and methods of the present invention for treatment of cancers.

"Stability" as used herein in refers to the stability of the drug in a composition deposited on a substrate in its final product form (e.g., stability of the drug in a coated stent). The term "stability" and/or "stable" in some embodiments is defined by 5% or less degradation of the drug in the final product form. The term stability in some embodiments is defined by 3% or less degradation of the drug in the final product form. The term stability in some embodiments is defined by 2% or less degradation of the drug in the final product form. The term stability in some embodiments is defined by 1% or less degradation of the drug in the final product form.

"Polymer" as used herein, refers to a series of repeating monomeric units that have been cross-linked or polymerized. Any suitable polymer can be used to carry out the present invention. It is possible that the polymers of the invention may also comprise two, three, four or more different polymers. In some embodiments of the invention only one polymer is used. In certain embodiments a combination of two polymers is used. Combinations of polymers can be in varying ratios, to provide compositions with differing properties. Polymers useful in the compositions, devices and methods of the present invention include, for example, stable or inert polymers, organic polymers, organic-inorganic copolymers, inorganic polymers, bioabsorbable, bioresorbable, resorbable, degradable, and biodegradable polymers. Those of skill in the art of polymer chemistry will be familiar with the different properties of polymeric compounds.

In some embodiments, the composition further comprises a polymer. In some embodiments, the active agent comprises a polymer. In some embodiments, the polymer comprises at least one of polyalkyl methacrylates, polyalkylene-co-vinyl acetates, polyalkylenes, polyurethanes, polyanhydrides, aliphatic polycarbonates, polyhydroxyalkanoates, silicone containing polymers, polyalkyl siloxanes, aliphatic polyesters, polyglycolides, polylactides, polylactide-co-glycolides, poly(e-caprolactone)s, polytetrahalooalkylenes, polystyrenes, poly(phosphasones), copolymers thereof, and combinations thereof.

In embodiments, the polymer is capable of becoming soft after implantation, for example, due to hydration, degradation or by a combination of hydration and degradation. In embodiments, the polymer is adapted to transfer, free, and/or dissociate from a delivery device when at the intervention site due to hydrolysis of the polymer. In various embodiments, the composition comprises a bioabsorbable polymer that is capable of resorbtion in at least one of: about 1 day, about 3 days, about 5 days, about 7 days, about 14 days, about 3 weeks, about 4 weeks, about 45 days, about 60 days, about 90 days, about 180 days, about 6 months, about 9 months, about 1 year, about 1 to about 2 days, about 1 to about 5 days, about 1 to about 2 weeks, about 2 to about 4 weeks, about 45 to about 60 days, about 45 to about 90 days, about 30 to about 90 days, about 60 to about 90 days, about 90 to about 180 days, about 60 to about 180 days, about 180 to about 365 days, about 6 months to about 9 months, about 9 months to about 12 months, about 9 months to about 15 months, and about 1 year to about 2 years.

Examples of polymers that may be used in the present invention include, but are not limited to polycarboxylic acids, cellulosic polymers, proteins, polypeptides, polyvinylpyrrolidone, maleic anhydride polymers, polyamides, polyvinyl alcohols, polyethylene oxides, glycosaminoglycans, polysaccharides, polyesters, aliphatic polyesters, polyurethanes, polystyrenes, copolymers, silicones, silicone containing polymers, polyalkyl siloxanes, polyorthoesters, polyanhydrides, copolymers of vinyl monomers, polycarbonates, polyethylenes, polypropytenes, polylactic acids, polylactides, polyglycolic acids, polyglycolides, polylactide-co-glycolides, polycaprolactones, poly(e-caprolactone)s, polyhydroxybutyrate valerates, polyacrylamides, polyethers, polyurethane dispersions, polyacrylates, acrylic latex dispersions, polyacrylic acid, polyalkyl methacrylates, polyalkylene-co-vinyl acetates, polyalkylenes, aliphatic polycarbonates polyhydroxyalkanoates, polytetrahalooalkylenes, poly(phosphasones), polytetrahalooalkylenes, poly (phosphasones), and mixtures, combinations, and copolymers thereof.

The polymers of the present invention may be natural or synthetic in origin, including gelatin, chitosan, dextrin, cyclodextrin, Poly(urethanes), Poly(siloxanes) or silicones, Poly(acrylates) such as [rho]oly(methyl methacrylate), poly (butyl methacrylate), and Poly(2-hydroxy ethyl methacrylate), Poly(vinyl alcohol) Poly(olefins) such as poly(ethylene), [rho]oly(isoprene), halogenated polymers such as Poly(tetrafluoroethylene)—and derivatives and copolymers such as those commonly sold as Teflon® products, Poly(vinylidine fluoride), Poly(vinyl acetate), Poly(vinyl pyrrolidone), Poly(acrylic acid), Polyacrylamide, Poly(ethylene-co-vinyl acetate), Poly(ethylene glycol), Poly(propylene glycol), Poly(methacrylic acid); etc.

Suitable polymers also include absorbable and/or resorbable polymers including the following, combinations, copolymers and derivatives of the following: Polylactides (PLA), Polyglycolides (PGA), PolyLactide-co-glycolides (PLGA), Polyanhydrides, Polyorthoesters, Poly(N-(2-hydroxypropyl) methacrylamide), Poly(l-aspartamide), including the derivatives DLPLA—poly(dl-lactide); LPLA—poly(l-lactide); PDO—poly(dioxanone); PGA-TMC—poly(glycolide-co-trimethylene carbonate); PGA-LPLA—poly(l-lactide-co-glycolide); PGA-DLPLA—poly(dl-lactide-co-glycolide); LPLA-DLPLA—poly(l-lactide-co-dl-lactide); and PDO-PGA-TMC—poly(glycolide-co-trimethylene carbonate-co-dioxanone), and combinations thereof.

"Copolymer" as used herein refers to a polymer being composed of two or more different monomers. A copolymer may also and/or alternatively refer to random, block, graft, copolymers known to those of skill in the art.

"Biocompatible" as used herein, refers to any material that does not cause injury or death to the animal or induce a serious adverse reaction in an animal when placed in intimate contact with the animal's tissues. Some relatively benign reaction such as acute inflammation and fibrotic encapsulation occur as part of any normal response to the presence of a foreign substance in contact with tissue. Serious adverse reactions include for example chronic inflammation, infection, excessive fibrotic tissue formation, necrotic cell death, or thrombosis. The terms "biocompatible" and "biocompatibility" when used herein are art-recognized and mean that the referent is neither itself toxic to a host (e.g., an animal or human), nor degrades (if it degrades) at a rate that produces byproducts (e.g., monomeric or oligomeric subunits or other byproducts) at toxic concentrations, causes chronic inflammation or irritation, or induces an immune reaction in the host. It is not necessary that any subject composition have a purity of 100% to be deemed biocompatible. Hence, a subject composition may comprise 99%, 98%, 97%, 96%, 95%, 90% 85%, 80%, 75% or even less of biocompatible agents, e.g., including polymers and other materials and excipients described herein, and still be biocompatible. "Non-biocompatible" as used herein, refers to any material that may cause injury or death to the animal or induce an adverse reaction in the animal when placed in intimate contact with the animal's tissues. Such adverse reactions are as noted above, for example.

The terms "bioabsorbable," "biodegradable," "bioerodible," "bioresorbable," and "resorbable" are art-recognized synonyms. These terms are used herein interchangeably. Bioabsorbable polymers typically differ from non-bioabsorbable polymers in that the former may be absorbed (e.g.; degraded) during use. In certain embodiments, such use involves in vivo use, such as in vivo therapy, and in other certain embodiments, such use involves in vitro use. In general, degradation attributable to biodegradability involves the degradation of a bioabsorbable polymer into its component subunits, or digestion, e.g., by a biochemical process, of the polymer into smaller, polymeric or non-polymeric subunits. In certain embodiments, biodegradation may occur by enzymatic mediation, degradation in the presence of water (hydrolysis) and/or other chemical species in the body, or both. The bioabsorbability of a polymer may be shown in-vitro as described herein or by methods known to one of skill in the art. An in-vitro test for bioabsorbability of a polymer does not require living cells or other biologic materials to show bioabsorption properties (e.g. degradation, digestion). Thus, resorbtion, resorption, absorption, absorbtion, erosion may also be used synonymously with the terms "bioabsorbable," "biodegradable," "bioerodible," and "bioresorbable." Mechanisms of degradation of a bioabsorbable polymer may include, but are not limited to, bulk degradation, surface erosion, and combinations thereof.

As used herein, the term "biodegradation" encompasses both general types of biodegradation. The degradation rate of a biodegradable polymer often depends in part on a variety of factors, including the chemical identity of the linkage responsible for any degradation, the molecular weight, crystallinity, biostability, and degree of cross-linking of such polymer, the physical characteristics (e.g., shape and size) of the implant, and the mode and location of administration. For example, the greater the molecular weight, the higher the degree of crystallinity, and/or the greater the biostability, the biodegradation of any bioabsorbable polymer is usually slower.

"Therapeutically desirable morphology" as used herein refers to the gross form and structure of the pharmaceutical agent, once included in the composition, so as to provide for optimal conditions of ex vivo storage, in vivo preservation and/or in vivo release. Such optimal conditions may include, but are not limited to increased shelf life (i.e., shelf stability), increased in vivo stability, good biocompatibility, good bioavailability or modified release rates. Typically, for the present invention, the desired morphology of a pharmaceutical agent would be crystalline or semi-crystalline or amorphous, although this may vary widely depending on many factors including, but not limited to, the nature of the pharmaceutical agent, the disease to be treated/prevented, the intended storage conditions for the composition prior to use or the location within the body of the interventional site. Preferably at least 10%, 20%, 30%, 40%, 50%, 60%, 70%, 80%, 90%, 95%, 97%, 98%, 99%, 99.5%, and/or 100% of the pharmaceutical agent is in crystalline or semi-crystalline form.

In some embodiments of the methods, compositions and/or devices provided herein, the macrolide immunosuppressive drug is at least 50% crystalline. In some embodiments, the macrolide immunosuppressive drug is at least 75% crystalline. In some embodiments, the macrolide immunosuppressive drug is at least 90% crystalline. In some embodiments of the compositions, methods and/or devices provided herein the macrolide immunosuppressive drug is at least 95% crystalline. In some embodiments of the compositions, methods and/or devices provided herein the macrolide immunosuppressive drug is at least 97% crystalline. In some embodiments of the compositions, methods and/or devices provided herein macrolide immunosuppressive drug is at least 98% crystalline. In some embodiments of the compositions, methods and/or devices provided herein the macrolide immunosuppressive drug is at least 99% crystalline.

In some embodiments of the compositions, methods and/or devices provided herein wherein the pharmaceutical agent is at least 50% crystalline. In some embodiments of the compositions, methods and/or devices provided herein the pharmaceutical agent is at least 75% crystalline. In some embodiments of the compositions, methods and/or devices provided herein the pharmaceutical agent is at least 90% crystalline. In some embodiments of the compositions, methods and/or devices provided herein the pharmaceutical agent is at least 95% crystalline. In some embodiments of the compositions, methods and/or devices provided herein the pharmaceutical agent is at least 97% crystalline. In some embodiments of the compositions, methods and/or devices provided herein pharmaceutical agent is at least 98% crystalline. In some embodiments of the compositions, methods and/or devices provided herein the pharmaceutical agent is at least 99% crystalline.

"Stabilizing agent" as used herein refers to any substance that maintains or enhances the stability of the biological agent. Ideally these stabilizing agents are classified as Generally Regarded As Safe (GRAS) materials by the US Food and Drug Administration (FDA). Examples of stabilizing agents include, but are not limited to carrier proteins, such as albumin, gelatin, metals or inorganic salts. Pharmaceutically acceptable excipients that may be present can further be found in the relevant literature, for example in the Handbook of Pharmaceutical Additives: An International Guide to More Than 6000 Products by Trade Name, Chemical, Function, and Manufacturer; Michael and Irene Ash (Eds.); Gower Publishing Ltd.; Aldershot, Hampshire, England, 1995.

"Intervention site" as used herein refers to the location in the body where the composition is intended to be delivered (by transfer from, freeing from, and/or dissociating from a delivery device). The intervention site can be any substance in the medium surrounding the delivery device, e.g., tissue, cartilage, a body fluid, etc. The intervention site can be the same as the treatment site, i.e., the substance to which the composition is delivered is the same tissue that requires treatment. Alternatively, the intervention site can be separate from the treatment site, requiring subsequent diffusion or transport of the pharmaceutical or other agent away from the intervention site.

"Compressed fluid" as used herein refers to a fluid of appreciable density (e.g., >0.2 g/cc) that is a gas at standard temperature and pressure. "Supercritical fluid," "near-critical fluid," "near-supercritical fluid," "critical fluid," "densified fluid," or "densified gas," as used herein refers to a compressed fluid under conditions wherein the temperature is at least 80% of the critical temperature of the fluid and the pressure is at least 50% of the critical pressure of the fluid, and/or a density of +50% of the critical density of the fluid.

Examples of substances that demonstrate supercritical or near critical behavior suitable for the present invention include, but are not limited to carbon dioxide, isobutylene, ammonia, water, methanol, ethanol, ethane, propane, butane, pentane, dimethyl ether, xenon, sulfur hexafluoride, halogenated and partially halogenated materials such as chlorofluorocarbons, hydrochlorofluorocarbons, hydrofluorocarbons, perfluorocarbons (such as perfluoromethane and perfluoropropane, chloroform, trichloro-fluoromethane, dichloro-difluoromethane, dichloro-tetrafluoroethane) and mixtures thereof. Preferably, the supercritical fluid is hexafluoropropane (FC-236EA), or 1,1,1,2,3,3-hexafluoropropane. Preferably, the supercritical fluid is hexafluoropropane (FC-236EA), or 1,1,1,2,3,3-hexafluoropropane for use in PLGA polymer compositions.

"Sintering" as used herein refers to the process by which parts of the polymer or the entire polymer becomes continuous (e.g., formation of a continuous polymer film). As discussed herein, the sintering process is controlled to produce a fully conformal continuous polymer (complete sintering) or to produce regions or domains of continuous composition while producing voids (discontinuities) in the polymer. As well, the sintering process is controlled such that some phase separation is obtained or maintained between different polymers (e.g., polymers A and B) and/or to produce phase separation between discrete polymer particles. Through the sintering process, the adhesive properties of the composition are improved to reduce flaking of detachment of the composition during manipulation in use. As described herein, in some embodiments, the sintering process is controlled to provide incomplete sintering of the polymer. In embodiments involving incomplete sintering, a polymer is formed with continuous domains, and voids, gaps, cavities, pores, channels or, interstices that provide space for sequestering a therapeutic agent which is released under controlled conditions. Depending on the nature of the polymer, the size of polymer particles and/or other polymer properties, a compressed gas, a densified gas, a near critical fluid or a super-critical fluid may be employed. In one example, carbon dioxide is used to prepare a composition comprising a polymer and a drug, using dry powder and RESS (described below) electrostatic composition processes. In another example, isobutylene is employed in the sintering process. In other examples a mixture of carbon dioxide and isobutylene is employed. In another example, 1,1,2,3,3-hexafluoropropane is employed in the sintering process.

When an amorphous material is heated to a temperature above its glass transition temperature, or when a crystalline material is heated to a temperature above a phase transition temperature, the molecules comprising the material are more mobile, which in turn means that they are more active and thus more prone to reactions such as oxidation. However, when an amorphous material is maintained at a temperature below its glass transition temperature, its molecules are substantially immobilized and thus less prone to reactions. Likewise, when a crystalline material is maintained at a temperature below its phase transition temperature, its molecules are substantially immobilized and thus less prone to reactions. Accordingly, processing drug components at mild conditions, such as the deposition and sintering conditions described herein, minimizes cross-reactions and degradation of the drug component. One type of reaction that is minimized by the processes of the invention relates to the ability to avoid conventional solvents which in turn minimizes-oxidation of drug, whether in amorphous, semi-crystalline, or crystalline form, by reducing exposure thereof to free radicals, residual solvents, protic materials, polar-protic materials, oxidation initiators, and autoxidation initiators.

"Rapid Expansion of Supercritical Solutions" or "RESS" as used herein involves the dissolution of a polymer into a compressed fluid, typically a supercritical fluid, followed by rapid expansion into a chamber at lower pressure, typically near atmospheric conditions. The rapid expansion of the supercritical fluid solution through a small opening, with its accompanying decrease in density, reduces the dissolution capacity of the fluid and results in the nucleation and growth of polymer particles. The atmosphere of the chamber is maintained in an electrically neutral state by maintaining an isolating "cloud" of gas in the chamber. Carbon dioxide, nitrogen, argon, helium, or other appropriate gas is employed to prevent electrical charge transfer from the substrate to the surrounding environment.

"Electrostatic Rapid Expansion of Supercritical Solutions" or "e-RESS" or "eRESS" as used herein refers to Electrostatic Capture as described herein combined with Rapid Expansion of Supercritical Solutions as described herein. In some embodiments, Electrostatic Rapid Expansion of Supercritical Solutions refers to Electrostatic capture as described in the art, e.g., in U.S. Pat. No. 6,756,084, "Electrostatic deposition of particles generated from rapid expansion of supercritical fluid solutions," incorporated herein by reference in its entirety.

"Solution Enhanced Dispersion of Supercritical Solutions" or "SEDS" as used herein involves a spray process for the generation of polymer particles, which are formed when a compressed fluid (e.g. supercritical fluid, preferably supercritical $CO_2$) is used as a diluent to a vehicle in which a polymer is dissolved (one that can dissolve both the polymer and the compressed fluid). The mixing of the compressed fluid diluent with the polymer-containing solution may be achieved by encounter of a first stream containing the polymer solution and a second stream containing the diluent compressed fluid, for example, within one spray nozzle or by the use of multiple spray nozzles. The solvent in the polymer solution may be one compound or a mixture of two or more ingredients and may be or comprise an alcohol (including diols, triols, etc.), ether, amine, ketone, carbonate, or alkanes, or hydrocarbon (aliphatic or aromatic) or may be a mixture of compounds, such as mixtures of alkanes, or mixtures of one or more alkanes in combination with additional compounds such as one or more alcohols, (e.g., from 0 or 0.1 to 5% of a Ci to $Ci_5$ alcohol, including diols, triols, etc.). See for example U.S. Pat. No. 6,669,785, incorporated herein by reference in its entirety. The solvent may optionally contain a surfactant, as also described in, e.g., U.S. Pat. No. 6,669,785.

In one embodiment of the SEDS process, a first stream of fluid comprising a polymer dissolved in a common solvent is co-sprayed with a second stream of compressed fluid. Polymer particles are produced as the second stream acts as a diluent that weakens the solvent in the polymer solution of the first stream. The now combined streams of fluid, along with the polymer particles, flow out of the nozzle assembly into a collection vessel. Control of particle size, particle size distribution, and morphology is achieved by tailoring the following process variables: temperature, pressure, solvent composition of the first stream, flow-rate of the first stream, flow-rate of the second stream, composition of the second stream (where soluble additives may be added to the compressed gas), and conditions of the capture vessel. Typically the capture vessel contains a fluid phase that is at least five to ten times (5-10×) atmospheric pressure.

"Electrostatic Dry Powder Composition" or "e-DPC" or "eDPC" as used herein refers to Electrostatic Capture as described herein combined with Dry Powder Composition. e-DPC deposits material (including, for example, polymer or impermeable dispersed solid) on a substrate as dry powder, using electrostatic capture to attract the powder particles to the substrate. Dry powder spraying ("Dry Powder Composition" or "DPC") is well known in the art, and dry powder spraying coupled with electrostatic capture has been described, for example in U.S. Pat. Nos. 5,470,603, 6,319,541, and 6,372,246, all incorporated herein by reference in their entirety. Methods for depositing compositions are described, e.g., in WO 2008/148013, "Polymer Films for Medical Device Composition," incorporated herein by reference in its entirety.

"Bulk properties" properties of a composition including a pharmaceutical or a biological agent that can be enhanced through the methods of the invention include for example: adhesion, smoothness, conformality, thickness, and compositional mixing.

"Electrostatically charged" or "electrical potential" or "electrostatic capture" as used herein refers to the collection of the spray-produced particles upon a substrate that has a different electrostatic potential than the sprayed particles. Thus, the substrate is at an attractive electronic potential with respect to the particles exiting, which results in the capture of the particles upon the substrate. i.e. the substrate and particles are oppositely charged, and the particles transport through the gaseous medium of the capture vessel onto the surface of the substrate is enhanced via electrostatic attraction. This may be achieved by charging the particles and grounding the substrate or conversely charging the substrate and grounding the particles, by charging the particles at one potential (e.g. negative charge) and charging the substrate at an opposite potential (e.g. positive charge), or by some other process, which would be easily envisaged by one of skill in the art of electrostatic capture.

"Depositing the active agent by an e-RESS, an e-SEDS, or an e-DPC process without electrically charging the substrate" as used herein refers to any of these processes as performed without intentionally electrically charging the substrate. It is understood that the substrate might become electrically charged unintentionally during any of these processes.

"Depositing the active agent by an e-RESS, an e-SEDS, or an e-DPC process without creating an electrical potential between the substrate and a composition apparatus" as used herein refers to any of these processes as performed without intentionally generating an electrical potential between the substrate and the composition apparatus. It is understood that electrical potential between the substrate and the composition apparatus might be generated unintentionally during any of these processes.

"Intimate mixture" as used herein, refers to two or more materials, compounds, or substances that are uniformly distributed or dispersed together.

"Layer" as used herein refers to a material covering a surface or forming an overlying part or segment. Two different layers may have overlapping portions whereby material from one layer may be in contact with material from another layer. Contact between materials of different layers can be measured by determining a distance between the materials. For example, Raman spectroscopy may be employed in identifying materials from two layers present in close proximity to each other.

While layers defined by uniform thickness and/or regular shape are contemplated herein, several embodiments described herein relate to layers having varying thickness and/or irregular shape. Material of one layer may extend into the space largely occupied by material of another layer. For example, in a composition having three layers formed in sequence as a first polymer layer, a pharmaceutical agent layer and a second polymer layer, material from the second polymer layer which is deposited last in this sequence may extend into the space largely occupied by material of the pharmaceutical agent layer whereby material from the second polymer layer may have contact with material from the pharmaceutical layer. It is also contemplated that material from the second polymer layer may extend through the entire layer largely occupied by pharmaceutical agent and contact material from the first polymer layer.

It should be noted however that contact between material from the second polymer layer (or the first polymer layer) and material from the pharmaceutical agent layer (e.g.; a pharmaceutical agent crystal particle or a portion thereof) does not necessarily imply formation of a mixture between the material from the first or second polymer layers and material from the pharmaceutical agent layer. In some embodiments, a layer may be defined by the physical three-dimensional space occupied by crystalline particles of a pharmaceutical agent (and/or biological agent). It is contemplated that such layer may or may not be continuous as physical space occupied by the crystal particles of pharmaceutical agents may be interrupted, for example, by polymer material from an adjacent polymer layer. An adjacent polymer layer may be a layer that is in physical proximity to be pharmaceutical agent particles in the pharmaceutical agent layer. Similarly, an adjacent layer may be the layer formed in a process step right before or right after the process step in which pharmaceutical agent particles are deposited to form the pharmaceutical agent layer.

As described herein, material deposition and layer formation provided herein are advantageous in that the pharmaceutical agent remains largely in crystalline form during the entire process. While the polymer particles and the pharmaceutical agent particles may be in contact, the layer formation process is controlled to avoid formation of a mixture between the pharmaceutical agent particles the polymer particles during formation of the composition.

In some embodiments, the composition comprises a plurality of layers deposited on the substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer.

In some embodiments of the compositions, methods and/or devices provided herein, the composition comprises a plurality of layers deposited on the substrate, wherein at least one of the layers comprises the active agent. In some embodiments, at least one of the layers comprises a polymer. In some embodiments, the polymer is bioabsorbable. In some embodiments, the active agent and the polymer are in the same layer, in separate layers, or form overlapping layers. In some embodiments, the composition comprises a plurality of layers deposited on the substrate, wherein at least one of the layers comprises the pharmaceutical agent. In some embodiments, the pharmaceutical agent and the polymer are in the same layer, in separate layers, or form overlapping layers. In some embodiments, the plurality of layers comprise five layers deposited as follows: a first polymer layer, a first active agent layer, a second polymer layer, a second active agent layer and a third polymer layer. In some embodiments, the plurality of layers comprise five layers deposited as follows: a first polymer layer, a first pharmaceutical agent layer, a second polymer layer, a second pharmaceutical agent layer and a third polymer layer. In some embodiments, the plurality of layers comprise five layers deposited as follows: a first polymer layer, a first active biological agent layer, a second polymer layer, a second active biological agent layer and a third polymer layer.

"Laminate composition" as used herein refers to a composition made up of two or more layers of material. Means for creating a laminate composition as described herein (e.g. a laminate composition comprising bioabsorbable polymer(s) and pharmaceutical agent) may include composition with drug and polymer as described herein (e-RESS, e-DPC, compressed-gas sintering). The process comprises performing multiple and sequential composition preparation steps (with sintering steps for polymer materials) wherein different materials may be deposited in each step, thus creating a laminated structure with a multitude of layers (at least 2 layers) including polymer layers and pharmaceutical agent layers to build the final composition.

"Substantially all of the composition" as used herein refers to at least about 50%, at least about 75%, at least about 85%, at least about 90%, at least about 95%, at least about 97%, and/or at least about 99% percent of the composition that was present prior to use.

"Delivering at least a portion" as used herein in the context of a composition and/or active agent at an intervention site refers to an amount and/or percentage of a composition and/or active agent that is delivered to an intervention site. In some embodiments, at least about 10%, at least about 20%, at least about 30%, at least about 50%, at least about 75%, at least about 85%, at least about 90%, at least about 95%, and/or at least about 99% of the composition and/or active agent is delivered to the intervention site.

In some embodiments, the composition is adapted to deliver at least about 10%, at least about 20%, at least about 30%, at least about 50%, at least about 75%, at least about 85%, at least about 90%, at least about 95%, and/or at least about 99% of the active agent to the intervention site.

In some embodiments, transferring at least a portion of the active agent comprises transferring at least about 3%, at least about 5%, at least about 10%, at least about 20%, at least about 30%, greater than 35%, at least about 50%, at least about 75%, at least about 85%, at least about 90%, at least about 95%, and/or at least about 99% of the active agent from the composition.

The term "adapted to transfer at least a portion" of the composition or active agent to an intervention site refers to a delivery device that is designed to transfer any portion of the composition or active agent to an intervention site.

The term "adapted to free" a portion of a composition and/or active agent from the substrate refers to a delivery device, composition, and/or substrate that is designed to free a certain percentage of the composition and/or active agent from the substrate.

A linear release may mean, depending on the embodiment, that upon analysis of elution data gathered according to methods noted herein or known to one of skill in the art using a least squares regression analysis of the data that there is an r-squared value of the best fit line that is at least 0.8 during the period noted, for example during any one or more of the following periods: from implantation until 30% of the agent is eluted, 50% of the agent is eluted, from implantation until 65% of the agent is eluted, from implantation until 20% of the agent is eluted, from implantation until 40% of the agent is eluted, from implantation until 45% of the agent is eluted, from implantation until 60% of the agent is eluted, from days 0 to 5, from days 0 to 9, from days 0 to 7, from days 0 to 14, from days 0 to 21, from days 0 to 28, from day 0 to one month, from days 1 to 5, from days 1 to 9, from days 1 to 7, from days 1 to 14, from days 1 to 21, from days 1 to 28, from day 1 to one month, and from day 1 to two months.

A linear release may mean, depending on the embodiment, that upon analysis of elution data gathered according to methods noted herein or known to one of skill in the art using a linear regression analysis of the data that there is an r-squared value of the best fit line that is at least 0.8 during the period noted, for example during any one or more of the following periods: from implantation until 30% of the agent is eluted, 50% of the agent is eluted, from implantation until 65% of the agent is eluted, from implantation until 20% of the agent is eluted, from implantation until 40% of the agent is eluted, from implantation until 45% of the agent is eluted, from implantation until 60% of the agent is eluted, from days 0 to 5, from days 0 to 9, from days 0 to 7, from days 0 to 14, from days 0 to 21, from days 0 to 28, from day 0 to one month, from days 1 to 5, from days 1 to 9, from days 1 to 7, from days 1 to 14, from days 1 to 21, from days 1 to 28, from day 1 to one month, and from day 1 to two months.

A linear release may mean, depending on the embodiment, that upon analysis of elution data gathered according to methods noted herein or known to one of skill in the art using curve-fitting of the data that there is a linear relationship between the time points and the elution data which has an r-squared value of the linear best fit line that is at least 0.8 during the period noted, for example during any one or more of the following periods: from implantation until 30% of the agent is eluted, 50% of the agent is eluted, from implantation until 65% of the agent is eluted, from implantation until 20% of the agent is eluted, from implantation until 40% of the agent is eluted, from implantation until 45% of the agent is eluted, from implantation until 60% of the agent is eluted, from days 0 to 5, from days 0 to 9, from days 0 to 7, from days 0 to 14, from days 0 to 21, from days 0 to 28, from day 0 to one month, from days 1 to 5, from days 1 to 9, from days 1 to 7, from days 1 to 14, from days 1 to 21, from days 1 to 28, from day 1 to one month, and from day 1 to two months.

A linear release may mean, depending on the embodiment, that upon analysis of elution data gathered according to methods noted herein or known to one of skill in the art using a least squares regression analysis of the data that there is an r-squared value of the best fit line that is at least 0.9 during the period noted, for example during any one or more of the following periods: from implantation until 30% of the agent is eluted, 50% of the agent is eluted, from implantation until 65% of the agent is eluted, from implantation until 20% of the agent is eluted, from implantation until 40% of the agent is eluted, from implantation until 45% of the agent is eluted, from implantation until 60% of the agent is eluted, from days 0 to 5, from days 0 to 9, from days 0 to 7, from days 0 to 14, from days 0 to 21, from days 0 to 28, from day 0 to one month, from days 1 to 5, from days 1 to 9, from days 1 to 7, from days 1 to 14, from days 1 to 21, from days 1 to 28, from day 1 to one month, and from day 1 to two months.

A linear release may mean, depending on the embodiment, that upon analysis of elution data gathered according to methods noted herein or known to one of skill in the art using a linear regression analysis of the data that there is an r-squared value of the best fit line that is at least 0.9 during the period noted, for example during any one or more of the following periods: from implantation until 30% of the agent is eluted, 50% of the agent is eluted, from implantation until 65% of the agent is eluted, from implantation until 20% of the agent is eluted, from implantation until 40% of the agent is eluted, from implantation until 45% of the agent is eluted, from implantation until 60% of the agent is eluted, from days 0 to 5, from days 0 to 9, from days 0 to 7, from days 0 to 14, from days 0 to 21, from days 0 to 28, from day 0 to one month, from days 1 to 5, from days 1 to 9, from days 1 to 7, from days 1 to 14, from days 1 to 21, from days 1 to 28, from day 1 to one month, and from day 1 to two months.

A linear release may mean, depending on the embodiment, that upon analysis of elution data gathered according to methods noted herein or known to one of skill in the art using curve-fitting of the data that there is a linear relationship between the time points and the elution data which has an r-squared value of the linear best fit line that is at least 0.9 during the period noted, for example during any one or more of the following periods: from implantation until 30% of the agent is eluted, 50% of the agent is eluted, from implantation until 65% of the agent is eluted, from implantation until 20% of the agent is eluted, from implantation until 40% of the agent is eluted, from implantation until 45% of the agent is eluted, from implantation until 60% of the agent is eluted, from days 0 to 5, from days 0 to 9, from days 0 to 7, from days 0 to 14, from days 0 to 21, from days 0 to 28, from day 0 to one month, from days 1 to 5, from days 1 to 9, from days 1 to 7, from days 1 to 14, from days 1 to 21, from days 1 to 28, from day 1 to one month, and from day 1 to two months.

The term SS refers to the following chemical substituent.

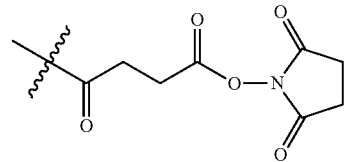 [SMILES: *C(=O)CCC(=O)ON1C(=O)CCC1=O]

The term SG refers to the following chemical substituent.

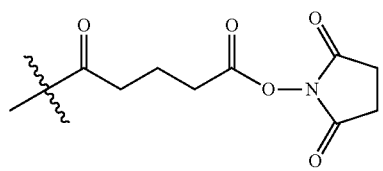 [SMILES: *C(=O)CCCC(=O)ON1C(=O)CCC1=O]

The term SA refers to the following chemical substituent.

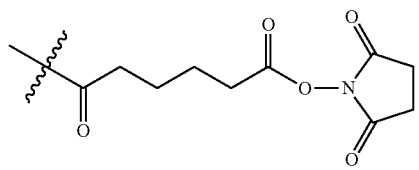 [SMILES: *C(=O)CCCCC(=O)ON1C(=O)CCC1=O]

The term SSub refers to the following chemical substituent.

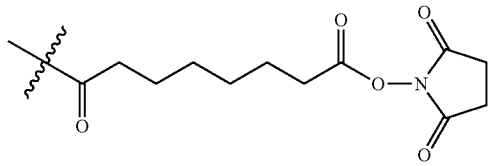 [SMILES: *C(=O)CCCCCCC(=O)ON1C(=O)CCC1=O]

The term SSeb refers to the following chemical substituent.

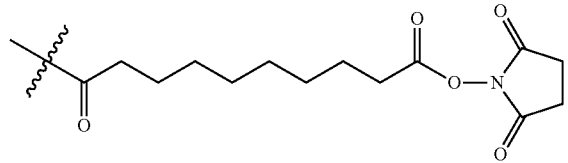 [SMILES: *C(=O)CCCCCCCCC(=O)ON1C(=O)CCC1=O]

Methods of Manufacturing Generally

In some embodiments, a composition is formed on the substrate by a process comprising depositing a polymer and/or the active agent by an e-RESS, an e-SEDS, or an e-DPC process. In some embodiments, the composition is formed on a substrate by a process comprising depositing the active agent by an e-RESS, an e-SEDS, or an e-DPC process without electrically charging the substrate. In some embodiments, the composition is formed on the substrate by a process comprising depositing the active agent on the substrate by an e-RESS, an e-SEDS, or an e-DPC process without creating an electrical potential between the substrate and a composition apparatus used to deposit the active agent. The composition is then released from the substrate and formed into a dosage form such as a composition suitable for injection; a coating for transdermal delivery device or formed into an oral dosage form.

Means for creating the bioabsorbable polymer(s)+drug(s) composition:

Provide a composition deposition substrate (such as a mandrel) for preparing the composition. The composition is released from the substrate for further processing and or packaging.

Spray-coat the composition-form with drug and polymer as is done in the described process (e-RESS, e-DPC, compressed-gas sintering).

Perform multiple and sequential composition-sintering steps where different materials may be deposited in each step, thus creating a laminated structure with a multitude of thin layers of drug(s), polymer(s) or drug+polymer that build the final composition.

Perform the deposition of polymer(s)+drug(s) laminates with the inclusion of a mask on the composition deposition substrate. Such a mask could be as simple as a non-conductive mandrel inserted through the internal diameter of the composition form. This masking could take place prior to any layers being added, or be purposefully inserted after several layers are deposited continuously around the entire composition-form.

Release the composition from the composition deposition substrate, and

Condition the composition for forming an injectable dosage form, a transdermal dosage form or a dosage form suitable for oral administration.

It is also contemplated that the compositions disclosed herein can be prepared by processing the polymer, the active pharmaceutical ingredient, the core if present and/or the pharmaceutically customary excipients by injection molding, extrusion, wet granulation, casting, spreading, spraying or compression to form compositions having the advantages described herein.

In some embodiments, the composition comprises a microstructure. In some embodiments, particles of the active agent are sequestered or encapsulated within the microstructure. In some embodiments, the microstructure comprises microchannels, micropores and/or microcavities. In some embodiments, the microstructure is selected to allow sustained release of the active agent. In some embodiments, the microstructure is selected to allow controlled release of the active agent.

Another advantage of the present invention is the ability to create a dosage form with a controlled (dialed-in) drug-release profile. Via the ability to have different materials in each layer of the laminate structure and the ability to control the location of drug(s) independently in these layers, the method enables a composition that could release drugs at very specific release profiles, programmed sequential and/or parallel release profiles. Also, the present invention allows controlled release of one drug without affecting the release of a second drug (or different doses of the same drug).

Provided herein is a method of forming a composition, wherein the composition comprises an active agent, the method comprising: providing the substrate; and forming the composition on at least a portion of the substrate by depositing the active agent by on the substrate by at least one of an e-RESS, an e-SEDS, and an e-DPC process, wherein forming the composition results in at least a portion of the composition being adapted to transfer from the substrate to prepare a dosage form containing the composition.

One embodiment provides a drug delivery composition comprising at least one hydrogel and at least one active agent; wherein the active agent is present in crystalline form and is embedded in the hydrogel.

Another embodiment provides the drug delivery composition wherein the composition indicates the presence of said pharmaceutical agent in crystalline form upon analysis by an analytical method selected from: (a) X-ray spectroscopy, (b) scanning electron microscopy (SEM), (c) Raman spectrum, (d) Differential Scanning calorimetry (DSC), (e) Wide Angle X-ray Scattering (WAXS) spectroscopy, and (f) wide angle radiation scattering spectroscopy.

Another embodiment provides the drug delivery composition wherein curing of the hydrogel occurs in-vivo.

Another embodiment provides the drug delivery composition wherein the composition is formed to provide a selected active agent controlled release profile. Another embodiment provides the drug delivery composition wherein the composition is in a form suitable for a mode of administration selected from: (a) injection, (b) intramuscular injection, (c) subcutaneous injection, (d) intrathecal injection, (e) intramuscular injection, (f) intraarticular injection, (g) intraperitoneal injection, (h) dermal administration, and (i) during a surgical procedure.

Another embodiment provides the drug delivery composition wherein the composition is adapted for delivery to at least one of: the front of the eye, the back of the eye, the location of a tumor, the location of cancerous cells, the location of cancerous tissue, the former location of cancerous tissue, the former location of cancerous cells, the former location of a tumor, the brain, a neurologic site, a location where inflammation is occurring, a location where inflammation may occur, a location where inflammation is expected to occur.

Another embodiment provides the drug delivery composition wherein the composition is adapted for dural repair.

Another embodiment provides the drug delivery composition wherein the composition is adapted to treat at least one of: intracranial aneurysms, tumors, and spinal disc disease.

Another embodiment provides the drug delivery composition wherein the composition is adapted to stop, slow, or prevent cervical spinal fluid leaks.

Another embodiment provides the drug delivery composition wherein the composition is capable of maintaining a seal under high pressures.

Another embodiment provides the drug delivery composition wherein the composition degrades as natural healing occurs.

Another embodiment provides the drug delivery composition wherein the composition acts as an adhesion barrier.

Another embodiment provides the drug delivery composition wherein the composition acts as a bandage.

Another embodiment provides the drug delivery composition wherein the composition is adapted to cover an opening in the eye and providing a protective barrier to the portion of the eye that is covered.

Another embodiment provides the drug delivery composition wherein the composition comprises voids.

Another embodiment provides the drug delivery composition wherein tissue ingrowth occurs in the voids as tissue heals.

Another embodiment provides the drug delivery composition wherein the composition is in the form of a mesh.

Another embodiment provides the drug delivery composition wherein the composition is adapted to seal tissue.

Another embodiment provides the drug delivery composition wherein the composition may be used in place of or in combination with tacks, staples, sutures, or O-rings in surgical procedures to seal tissue.

Another embodiment provides the drug delivery composition wherein the composition bioabsorbs or degrades as tissue grows into the voids of the mesh and into areas where the hydrogel has been degraded or absorbed.

Another embodiment provides the drug delivery composition wherein the hydrogel is biodegradable.

Another embodiment provides the drug delivery composition wherein the hydrogel is anti-microbial.

Another embodiment provides the drug delivery composition wherein the biologically active agent is encapsulated in microparticles or nanoparticles.

Another embodiment provides the drug delivery composition wherein the composition further comprises one or more agents that modulate the viscosity of the composition.

Another embodiment provides the drug delivery composition wherein the agent that modulates the viscosity of the composition lowers the viscosity of the composition at room temperature.

Another embodiment provides the drug delivery composition wherein the agent that modulates the viscosity of the composition increases the viscosity of the composition at temperatures above 35° C.

Another embodiment provides the drug delivery composition wherein the active agent is selected from rapamycin, a prodrug, a derivative, an analog, a hydrate, an ester, and a salt thereof.

Another embodiment provides the drug delivery composition wherein the active agent is selected from one or more of sirolimus, everolimus, zotarolimus and biolimus.

Another embodiment provides the drug delivery composition wherein the active agent comprises a macrolide immunosuppressive (limus) drug.

Another embodiment provides the drug delivery composition wherein the active agent is a macrolide immunosuppressive drug selected from one or more of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycar-bonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and salts, derivatives, polymorphs, isomers, racemates, diastereoisomers, prodrugs, hydrate, ester, or analogs thereof.

Another embodiment provides the drug delivery composition wherein the active agent is at least 50% crystalline, at least 75% crystalline, or at least 90% crystalline.

Another embodiment provides the drug delivery composition wherein the hydrogel comprises a polymer.

Another embodiment provides the drug delivery composition wherein the polymer comprises a PLGA copolymer.

Another embodiment provides the drug delivery composition wherein the polymer comprises a first PLGA copolymer with a ratio of about 40:60 to about 60:40 and a second PLGA copolymer with a ratio of about 60:40 to about 90:10.

Another embodiment provides the drug delivery composition wherein the polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

Another embodiment provides the drug delivery composition wherein between 25% and 45% of the total amount of active agent in the composition is released after 24 hours in vitro release in a 1:1 spectroscopic grade ethanol/phosphate buffer saline at pH 7.4 and 37° C.; wherein the amount of the active agent released is determined by measuring UV absorption at 278 nm by a diode array spectrometer.

Another embodiment provides the drug delivery composition wherein the composition is suitable for use in a mode of administration selected from: (a) injection into the bladder to treat bladder cancer, (b) injection into the prostate gland to treat prostate cancer, (c) injection into or near the vitreous humor of the eye to treat ocular disease, and (d) injection into the nasal turbinates to treat chronic sinusitis.

Another embodiment provides the drug delivery composition wherein the composition is suitable for injection into an intervention site wherein the intervention site is selected from: (a) the wall of a body cavity, (b) the wall of a body cavity resulting from partial or complete tumor removal, (c) a cannulized site within a subject, (d) a nasal turbinate, (e) within the reproductive system of a subject, (f) within the urinary system of a subject, (g) located at a tumor site, (f) a location in the ear, (g) a location in the esophagus, (h) a location in the larynx, (i) a location of an injury, (j) an infection site, (k) a surgery site, (l) an ocular site, (m) an inflammatory site, or (n) an arthritic joint.

Another embodiment provides the drug delivery composition wherein the composition is adapted to treat an ailment selected from: (a) an ailment of the reproductive system, (b) an ailment of the urinary system.

Another embodiment provides the drug delivery composition wherein the composition is adapted for delivery to at least one of an intervention site, an infection site, and an inflammatory site.

Another embodiment provides the drug delivery composition adapted for delivery to an intervention site wherein the intervention site is located in the urinary system of a subject.

Another embodiment provides the drug delivery composition adapted for delivery to an intervention site wherein the intervention site is located at a tumor site.

Another embodiment provides the drug delivery composition adapted for delivery to a tumor site wherein the tumor site is where a tumor is located.

Another embodiment provides the drug delivery composition adapted for delivery to a tumor site wherein the tumor site is where a tumor was located prior to removal and/or shrinkage of the tumor.

Another embodiment provides the drug delivery composition adapted for delivery to an intervention site wherein the intervention site is located in the ear.

Another embodiment provides the drug delivery composition adapted for delivery to an intervention site wherein the intervention site is located in the esophagus.

Another embodiment provides the drug delivery composition adapted for delivery to an intervention site wherein the intervention site is located in the larynx.

Another embodiment provides the drug delivery composition adapted for delivery to an intervention site wherein the intervention site is a location of an injury.

Another embodiment provides the drug delivery composition adapted for delivery to an intervention site wherein the intervention site is an infection site.

Another embodiment provides the drug delivery composition wherein the composition is adapted for delivery to an inflammatory site wherein the inflammatory site is a site wherein inflammation may occur, and wherein the active agent is capable of substantially preventing the inflammation.

Another embodiment provides the drug delivery composition wherein the composition is adapted for delivery to an inflammatory site wherein the inflammatory site is a site wherein inflammation may occur, and wherein the active agent is capable of substantially reducing the inflammation.

Another embodiment provides the drug delivery composition wherein the composition is adapted for delivery to an infection site wherein the infection site is a site wherein an infection may occur, and wherein the active agent is capable of substantially preventing the infection.

Another embodiment provides the drug delivery composition wherein the composition is adapted for delivery to an infection site wherein the infection site is a site wherein an infection has occurred, and wherein the active agent is capable of slowing spread of the infection.

Another embodiment provides the drug delivery composition wherein the composition is adapted for delivery to an intervention site wherein the intervention site is an ocular site.

Another embodiment provides the drug delivery composition wherein the composition is capable of at least one of: retarding healing, delaying healing, and preventing healing.

Another embodiment provides the drug delivery composition wherein the composition is capable of at least one of: retarding, delaying, and preventing the inflammatory phase of healing.

Another embodiment provides the drug delivery composition wherein the composition is capable of at least one of: retarding, delaying, and preventing the proliferative phase of healing.

Another embodiment provides the drug delivery composition wherein the active agent and the polymer are in the same layer, in separate layers, or form overlapping layers.

Another embodiment provides the drug delivery composition wherein the active agent is uniformly dispersed within the composition.

Another embodiment provides the drug delivery composition wherein the active agent release profile is a linear release profile until 30% of the total content of active agent is released.

Another embodiment provides the drug delivery composition wherein the active agent release profile is a linear release profile until 50% of the total content of active agent is released.

Another embodiment provides the drug delivery composition wherein the composition releases the active agent at a selected therapeutic level over a period of at least 48 hours after injection.

Another embodiment provides the drug delivery composition wherein the composition reduces or eliminates adverse toxic effect associated with oral formulation of the active agent.

Another embodiment provides the drug delivery composition wherein the composition is suitable for intramuscular injection or intraperitoneal injection.

Another embodiment provides the drug delivery composition wherein the active agent is delivered transdermally from the composition at a selected active agent release profile.

Another embodiment provides the transdermal drug delivery composition further comprising a microprotrusion member having a plurality of stratum corneum piercing microprotrusions thereon and being adapted for piercing the stratum corneum to improve transdermal flux of the composition.

Another embodiment provides the transdermal drug delivery composition wherein the composition releases the active agent at a selected therapeutic level over a period of at least 48 hours after application of the composition.

Another embodiment provides the transdermal drug delivery composition wherein the composition reduces or eliminates adverse toxic effect associated with oral formulation of the active agent.

Another embodiment provides the drug delivery composition wherein the composition is adapted for delivery intra-articularly.

Another embodiment provides the drug delivery composition wherein the hydrogel comprises a hydrogel composition that is derived from an activated polyalkylene glycol diacid derivative and a crosslinking agent.

Another embodiment provides the drug delivery composition comprising a hydrogel composition wherein the activated polyalkylene diacid derivative is represented by formula (I):

$$\underset{O}{\overset{O}{\underset{\|}{N}}}-O-\underset{R}{\overset{O}{\underset{R}{C}}}\underset{m}{\overset{}{\left(\right)}}O-(CH_2CH_2O)_w-\underset{R}{\overset{O}{\underset{R}{C}}}\underset{m}{\overset{}{\left(\right)}}O-\underset{O}{\overset{O}{\underset{\|}{N}}}$$

wherein, independently for each occurrence, R is H or lower alkyl; m is 2-20 inclusive; and w is 5 to 1,000 inclusive.

Another embodiment provides the drug delivery composition comprising a hydrogel composition wherein the crosslinking agent is a polyalkyleneimine or trilysine.

Another embodiment provides the drug delivery composition comprising a hydrogel composition wherein the crosslinking agent is polyethyleneimine having a molecular weight of about 2000.

Another embodiment provides the drug delivery composition comprising a hydrogel composition wherein the crosslinking agent is trilysine.

Another embodiment provides the drug delivery composition comprising a hydrogel component of formula (I) wherein m is 2-10 inclusive.

Another embodiment provides the drug delivery composition comprising a hydrogel component of formula (I) wherein m is 2.

Another embodiment provides the drug delivery composition comprising a hydrogel component of formula (I) wherein m is 3.

Another embodiment provides the drug delivery composition comprising a hydrogel component of formula (I) wherein m is 4.

Another embodiment provides the drug delivery composition comprising a hydrogel component of formula (I) wherein m is 6.

Another embodiment provides the drug delivery composition comprising a hydrogel component of formula (I) wherein m is 8.

Another embodiment provides the drug delivery composition comprising a hydrogel component of formula (I) wherein w is 20 to 120 inclusive.

Another embodiment provides the drug delivery composition comprising a hydrogel component of formula (I) wherein w is 120 to 250 inclusive.

Another embodiment provides the drug delivery composition comprising a hydrogel composition wherein the activated polyalkylene glycol diacid derivative is $R-PEG_n-R$; wherein n represents the number average molecular weight of the PEG and is about 2000 to about 12,000 inclusive; and R is SS, SG, SA, SSub, or SSeb.

Another embodiment provides the drug delivery composition comprising a hydrogel composition wherein the activated polyalkylene glycol diacid derivative is $PEG_{3350}$-$(SS)_2$.

Another embodiment provides the drug delivery composition comprising a hydrogel composition wherein the activated polyalkylene glycol diacid derivative is (SS)-$PEG_{3350}$-(SS).

Another embodiment provides the drug delivery composition comprising a hydrogel composition wherein the activated polyalkylene glycol diacid derivative is $PEG_{3350}$-$(SG)_2$.

Another embodiment provides the drug delivery composition comprising a hydrogel composition wherein the activated polyalkylene glycol diacid derivative is (SG)-$PEG_{3350}$-(SG).

Another embodiment provides the drug delivery composition comprising a hydrogel composition wherein the activated polyalkylene glycol diacid derivative is $PEG_{3350}$-$(SA)_2$.

Another embodiment provides the drug delivery composition comprising a hydrogel composition wherein the activated polyalkylene glycol diacid derivative is (SA)-$PEG_{3350}$-(SA).

Another embodiment provides the drug delivery composition comprising a hydrogel composition wherein the activated polyalkylene glycol diacid derivative is $PEG_{3350}$-$(SSeb)_2$.

Another embodiment provides the drug delivery composition comprising a hydrogel composition wherein the activated polyalkylene glycol diacid derivative is (SSeb)-$PEG_{3350}$-(SSeb).

Another embodiment provides the drug delivery composition comprising a hydrogel composition wherein the activated polyalkylene glycol diacid derivative is $PEG_{3350}$-$(SSub)_2$.

Another embodiment provides the drug delivery composition comprising a hydrogel composition wherein the activated polyalkylene glycol diacid derivative is (SSub)-$PEG_{3350}$-(SSub).

Another embodiment provides the drug delivery composition comprising a hydrogel component wherein the weight percent crosslinker is between about 5% and about 50%.

Another embodiment provides the drug delivery composition comprising a hydrogel component wherein the weight percent crosslinker is about 15%.

Another embodiment provides the drug delivery composition comprising a hydrogel component wherein the ratio of activated esters on the polyalkylene glycol diacid derivatives to primary amines on the crosslinking agent is in the range from about 0.10:1 to about 10:1.

Another embodiment provides the drug delivery composition comprising a hydrogel component wherein the ratio of activated esters on the polyalkylene glycol diacid derivatives to primary amines on the crosslinking agent is in the range from about 0.75:1 to about 1.3:1.

Another embodiment provides the drug delivery composition comprising a hydrogel component wherein R is methyl or H.

Another embodiment provides the drug delivery composition comprising a hydrogel component wherein R is H.

EXAMPLES

The following examples are provided to illustrate selected embodiments. They should not be considered as limiting the scope of the invention, but merely as being illustrative and representative thereof. For each example listed herein, multiple analytical techniques may be provided. Any single technique of the multiple techniques listed may be sufficient to show the parameter and/or characteristic being tested, or any combination of techniques may be used to show such parameter and/or characteristic. Those skilled in the art will be familiar with a wide range of analytical techniques for the characterization of drug/polymer compositions. Techniques presented here, but not limited to, may be used to additionally and/or alternatively characterize specific properties of the compositions with variations and adjustments employed which would be obvious to those skilled in the art.

Sample Preparation

Generally speaking, compositions prepared for in-vivo models are prepared as herein. Nevertheless, modifications for a given analytical method are presented within the examples shown, and/or would be obvious to one having skill in the art. Thus, numerous variations, changes, and substitutions will now occur to those skilled in the art without departing from the invention. It should be understood that various alternatives to the embodiments of the invention described herein and examples provided may be employed in practicing the invention and showing the parameters and/or characteristics described.

Compositions for Controlled Release Dosage Forms

In some examples, the composition process is PDPDP (Polymer, sinter, Drug, Polymer, sinter, Drug, Polymer, sinter) using deposition of drug in dry powder form and deposition of polymer particles by RESS methods and equipment described herein. In the illustrations herein, resulting in a 3-layer composition comprising polymer (for example, PLGA) in the first layer, drug (for example, rapamycin) in a second layer and polymer in the third layer, where a portion of the third layer is substantially drug free (e.g. a sub-layer within the third layer having a thickness equal to a fraction of the thickness of the third layer). As described layer, the middle layer (or drug layer) may be overlapping with one or both first (polymer) and third (polymer) layer. The overlap between the drug layer and the polymer layers is defined by extension of polymer material into physical space largely occupied by the drug. The overlap between the drug and polymer layers may relate to partial packing of the drug particles during the formation of the drug layer. When crystal drug particles are deposited on top of the first polymer layer, voids and or gaps may remain between dry crystal particles. The voids and gaps are available to be occupied by particles deposited during the formation of the third (polymer) layer. Some of the particles from the third (polymer) layer may rest in the vicinity of drug particles in the second (drug) layer. When the sintering step is completed for the third (polymer) layer, the third polymer layer particles fuse to form a continuous film that forms the third (polymer) layer. In some embodiments, the third (polymer) layer however will have a portion along the longitudinal axis of the stent whereby the portion is free of contacts between polymer material and drug particles. The portion of the third layer that is substantially of contact with drug particles can be as thin as 1 nanometer.

The composition may be analyzed (for example, for analysis of crystallinity of the active agent). The composition may be sliced into sections which may be visualized using the surface composition techniques presented herein or other techniques known in the art for surface composition analysis (or other characteristics, active agent distribution, for example).

The compositions described herein allow for the production of a highly concentrated, sustained release formulation of rapamycin with enhanced drug stability and controlled release capabilities. Therapy can take the form of injectable or implantable drug depots, transdermal or mucosal patches, suppositories or coatings on medical implants as well as more traditional oral forms of administration.

Rapamycin (also known as Sirolimus) forms a complex with FK Binding Protein-12 (FKBP-12). This complex binds to and inhibits activation of a key regulatory kinase, mammalian Target of Rapamycin (mTOR). This is believed to suppress cytokine-driven cell proliferation, inhibiting cell cycle progression from the G1 to S phase. Rapamycin can be used to treat a wide variety of diseases brought on by uncontrolled cell growth due to the importance of mTOR in regulating cell proliferation in many different types of cells.

The clinical utility of Rapamycin, currently formulated as Rapamune® oral tablets or solution, is limited by its poor aqueous solubility, low bioavailability (<14%), high protein binding and extensive hepatic biotransformation. Once daily oral dosing results in non-steady state pharmacokinetics requiring close monitoring of serum peak and trough levels to maintain drug in a therapeutic range. Depending on the immunosuppressive dose used (2 or 5 mg daily), blood concentrations can range from 6-50 ng/ml. A controlled release formulation that can deliver drug at a constant rate could improve drug effectiveness and reduce the risk of toxicity. Delivery of drug from implanted depots or other types of reservoir technologies could improve bioavailability and provide delivery closer to a selected target.

The following disease targets are known to be susceptible to mTOR inhibitors such as rapamycin. These pathologies might be better treated with a therapeutic modality that provides a more constant inhibition of mTOR activity or an increase in the local concentration of that inhibitor.

Illustrative Disease Targets:

Plas D R and Thomas G, "Tubers and tumors: rapamycin therapy for benign and malignant tumors", Curr Opin Cell Bio 21: 230-236, (2009) lists the following targets: Immunosuppression following organ transplantation, prevention of restenosis following cardiovascular intervention, treatment of phakomatosis and harmartomatous diseases and treatment of cancers, particularly those linked to Akt activation such as renal cell carcinoma, glioblastoma and prostate cancer.

Immunosuppression

The immunosuppressive activity of rapamycin is due, in part, from its ability to inhibit the cytokine mediated proliferation of T- and B-lymphocytes, both of which play major roles in graft rejection. In fact, rapamycin has been shown to affect the expression of hundreds of genes in these lymphocytes. Activation of lymphocytes and transplant allograft rejection occurs both as a systemic and local response to the graft. Local delivery of immunosuppressive therapy in the early transplantation period directly into the graft is, therefore, a possible way to prevent rejection and reduce the systemic dose and the accompanying systemic adverse effects of these drugs.

Preclinical evaluation of two-week continuous intraportal administration of immunosuppressant therapy was evaluated in a model of canine liver transplantation. The result was increased levels of therapeutic agent in the graft and dramatically increased survival compared to animals given comparable amounts of systemic therapy.

Another example of where local immunosuppression provides clear benefit is with corneal transplantation. There is a "high risk" patient population in which up to 60% of corneal allografts are rejected despite the use of topical steroids. The failure in suppression of graft rejection usually results from the inability to achieve effective drug concentrations in the cornea and anterior chamber. Recently a novel implant technology using nanoparticles loaded with rapamycin has been shown to demonstrate improved graft survival in a rabbit model of corneal transplantation.

While the currently available dosage forms of rapamycin reduce the risk of transplant rejection, it is clear from these examples that sustained release of drug into or near the graft might provide additional benefit, particularly in the first few weeks after implant. Continuous local infusion of rapamycin through an extracorporeal catheter might increase the risk of infection or other morbidity. The technology disclosed herein offers a potentially safer solution with the local implantation of biodegradable drug depot capable of sustaining release of active drug at a constant rate for a period of approximately two weeks.

Tuberous Sclerosis

Tuberous sclerosis is an autosomal dominant, multi-system tumor disorder affecting brain, kidneys, lungs, heart and skin. The disease occurs as the result of a mutation in either the TSC1 or the TSC2 genes that, under normal circumstances, produce proteins that bind to form a tumor suppressor complex. Failure of the tumor suppressor complex to function results in constitutively active mTOR Inhibitors of mTOR such as rapamycin are used, therefore to treat tuberous sclerosis. Systemic rapamycin therapy reduces tumors but the response is incomplete, often temporary and associated with significant, if tolerable, side effects. More effective treatment strategies are sought.

One strategy for improved treatment is the local application of rapamycin to tumor sites to increase the concentration of mTOR inhibitor within the tumor. Topical delivery of rapamycin by application of a patch near the skin lesions resulted in reduced tumor growth in a mouse model of tuberous sclerosis. The technology disclosed herein could be used to generate dermal drug delivery patches with the capacity to deliver active rapamycin for extended periods.

Other Cancers

Rapamycin's target, mTOR, plays an important role in the proliferation of numerous cell types including many cancer cell types. As is the case with immunosuppression, improved effectiveness and reduced toxicity could be achieved with a drug delivery technology capable of sustained, controlled release of drug that would maintain optimal therapeutic serum and tumor levels of anti-proliferative drug. Specifically, with regard to adenocarcinomas it is known that continuous infusion of rapamycin results in significantly greater tumor inhibition than daily administration. Although rapamycin and other mTOR inhibitors have the potential to greatly impact tumor growth, progression and resistance, they have enjoyed only modest success in many clinical trials. This may be due to less than optimal drug dosing or the activity of negative feedback loops that limit drug effect.

To provide additional and/or improved anti-cancer therapy, the technology disclosed herein could be used to generate a rapamycin-delivery implant capable of providing sustained release of active drug either systemically in the case of metastatic disease or more directly into a solid tumor. In addition, since mTOR dysregulation is known to be an important element of a number of different brain tumors such as neurofibromatosis and the brain tumors from tuberous sclerosis, a form of rapamycin delivery that could be implanted beyond the blood brain barrier is potentially advantageous.

Anti-TNFα

One of rapamycin's myriad of cellular effects is the inhibition of Tumor Necrosis Factor-α (TNFα) release from vascular smooth muscle cells. TNFα is a proinflammatory, prothrombotic cytokine elevated in response to endogenous disease such as arthritis and atherosclerosis and also released in response to vascular injury, particularly in response to a foreign body. Part of the rapamycin-eluting stent's antirestenotic effectiveness may be due to its ability to inhibit TNFα release. Other types of medical implants also cause release of TNFα. The release of this cytokine can aggravate on-going disease and also result in damage to the implant itself. For example, in the case of joint replacements such as hip or knee arthroplasty, wear debris from the prosthesis can initiate an inflammatory response including release of TNFα which in turn leads to recruitment of activated osteoclasts that can degrade the bone-implant interface.

A novel solution to this issue would be a surface coating on the prosthetic that released rapamycin as an inhibitor of TNFα (in addition to its other anti-inflammatory effects). The composition formation technology disclosed herein could lend itself well to this type of application.

Autism and Alzheimer's Disease

Cellular events such as phosphorylation of neural proteins are partially responsible for the processing of neural input and the generation of memories. The kinase, mTOR, acts as a "node of convergence" in which many different types of signals are translated into phosphorylation events. Although disorders like autism can arise from multiple genetic alterations, 5-10% of these directly involve mTOR signaling or translational control. mTOR dysregulation is also a characteristic of Alzheimer's disease.

Although rapamycin is a potent means to inhibit mTOR, its use to treat these complex diseases is still highly experimental. mTOR is not a simple "on/off" switch and both too much or too little mTOR activity can negatively impact neuronal signaling. In addition, there is evidence that even within a single cell proper functioning of mTOR may involve increased activity in one compartment and decreased activity in another. While intriguing, much more will have to be learned before undertaking the optimized delivery of rapamycin to treat these types of diseases.

The methods disclosed herein can produce drug delivery products comprised of stable, concentrated rapamycin that elutes from a biodegradable matrix at a constant rate for a prolonged period of time. Drug delivery kinetics can be varied based on critical formulation parameters. The use of these types of compositions can potentially provide both novel and better optimized therapeutic options to treat a wide variety of disease states.

Injectable Dosage Forms

This example will use a rodent (rat) model to demonstrate that the injectable drug deposition technology results in more constant rapamycin blood levels than seen with once-daily oral dosing. A rat model of cardiac allograft transplantation has been used previously to assess the effectiveness of continuous intravenous infusion of rapamycin compared to oral dosing. This previous study provides data on how blood levels of rapamycin correlate with anti-rejection effectiveness and establishes an effective dose range for the rat based on that data.

Objective:

This study will compare the injectable drug deposition technology to once-daily oral dosing of rapamycin with regard to maintaining a more constant level of rapamycin in the blood. Three different doses of injectable rapamycin will be used to begin to develop an understanding of the pharmacokinetics of this mode of administration. The oral dose used will be 4.9 mg/kg/day. This has been shown to result in prolonged allograft survival in 70% of rats treated. As this study is only assessing the blood levels of drug, transplantation of allograft tissue is not needed.

Method:

Adult male Wistar Furth rats, 7-9 weeks old will be used to better correlate with results from previous studies evaluating rapamycin dosing and effectiveness. An injectable formulation of rapamycin will be prepared as described in the previous above under Sample Preparation. The formulation will be modified to allow for three different doses of drug to be delivered from a depot created with approximately a 1 ml volume of injectate. Each formulation will be loaded into an individual syringe and injected into the subcutaneous space of a rat (n=3 for each formulation). Three rats will receive once daily dosing of rapamycin (4.9 mg/kg) by oral gavage.

The duration of the study will be 14 days with 0.3 ml blood draws from either a tail vein or indwelling catheter every other day immediately before and 1.5 hours after daily dosing in the animals receiving oral drug and once each day from animals that received a injectable dose of drug at the beginning of the study. The amount of blood drawn may change based on results of preliminary studies to ascertain the minimum sample volume needed to accurately assess drug content. Blood concentrations of rapamycin will be determined based on established methods.

The data collected will demonstrate the variability in blood drug levels between peak (1.5 hours post oral dosing) and trough (24 hours after once daily dosing) values and also from day to day. The hypothesis to be tested is whether an injectable depot of drug using the formulations disclosed herein will result in less variability in systemic drug levels over time. It is anticipated that the drug-polymer formulation will allow for a relatively constant rate of drug delivery. This data will also allow for a determination of the amount and duration of drug delivery from a single injectable depot containing 1 ml of a specific formulation. Variability of drug levels will be assessed using appropriate statistical analyses.

The foregoing is illustrative of the present invention, and is not to be construed as limiting thereof. While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A drug delivery composition comprising:
   a bioabsorbable polymer; and
   an active agent, the active agent including a crystalline limus drug not encapsulated in microparticles or nanoparticles,
   wherein the composition is formed to provide a selected active agent controlled release profile, in a dosage form created by a plurality of polymer and active agent layers and independent of other substrates and wherein the composition comprises five layers as follows: a first polymer layer, a first active agent layer, a second polymer layer, a second active agent layer and a third polymer layer.

2. The composition of claim 1, wherein the composition is in a dosage form capable of being administered through a mode of administration selected from: (a) injection, (b) intramuscular injection, (c) subcutaneous injection, (d) intrathecal injection, (e) intramuscular injection, (f) intraarticular injection, (g) intraperitoneal injection and (h) during a surgical procedure.

3. The composition of claim 1, wherein the active agent is a macrolide immunosuppressive drug selected from the group consisting of rapamycin, biolimus (biolimus A9), 40-O-(2-Hydroxyethyl)rapamycin (everolimus), 40-O-Benzyl-rapamycin, 40-O-(4'-Hydroxymethyl)benzyl-rapamycin, 40-O-[4'-(1,2-Dihydroxyethyl)]benzyl-rapamycin, 40-O-Allyl-rapamycin, 40-O-[3'-(2,2-Dimethyl-1,3-dioxolan-4(S)-yl)-prop-2'-en-1'-yl]-rapamycin, (2':E,4'S)-40-O-(4',5'-Dihydroxypent-2'-en-1'-yl)-rapamycin, 40-O-(2-Hydroxy)ethoxycarbonylmethyl-rapamycin, 40-O-(3-Hydroxy)propyl-rapamycin, 40-O-(6-Hydroxy)hexyl-rapamycin, 40-O-[2-(2-Hydroxy)ethoxy]ethyl-rapamycin, 40-O-[(3S)-2,2-Dimethyldioxolan-3-yl]methyl-rapamycin, 40-O-[(2S)-2,3-Dihydroxyprop-1-yl]-rapamycin, 40-O-(2-Acetoxy)ethyl-rapamycin, 40-O-(2-Nicotinoyloxy)ethyl-rapamycin, 40-O-[2-(N-Morpholino)acetoxy]ethyl-rapamycin, 40-O-(2-N-Imidazolylacetoxy)ethyl-rapamycin, 40-O-[2-(N-Methyl-N'-piperazinyl)acetoxy]ethyl-rapamycin, 39-O-Desmethyl-39,40-O,O-ethylene-rapamycin, (26R)-26-Dihydro-40-O-(2-hydroxy)ethyl-rapamycin, 28-O-Methyl-rapamycin, 40-O-(2-Aminoethyl)-rapamycin, 40-O-(2-Acetaminoethyl)-rapamycin, 40-O-(2-Nicotinamidoethyl)-rapamycin, 40-O-(2-(N-Methyl-imidazo-2'-ylcarbethoxamido)ethyl)-rapamycin, 40-O-(2-Ethoxycarbonylaminoethyl)-rapamycin, 40-O-(2-Tolylsulfonamidoethyl)-rapamycin, 40-O-[2-(4',5'-Dicarboethoxy-1',2',3'-triazol-1'-yl)-ethyl]-rapamycin, 42-Epi-(tetrazolyl)rapamycin (tacrolimus), 42-[3-hydroxy-2-(hydroxymethyl)-2-methylpropanoate]rapamycin (temsirolimus), (42S)-42-Deoxy-42-(1H-tetrazol-1-yl)-rapamycin (zotarolimus), and combinations thereof.

4. The composition of claim 1, wherein the active agent is at least 50% crystalline, at least 75% crystalline, or at least 90% crystalline.

5. The composition of claim 1, wherein the composition comprises a first PLGA copolymer with a ratio of about 40:60 to about 60:40 and a second PLGA copolymer with a ratio of about 60:40 to about 90:10.

6. The composition of claim 1, wherein the bioabsorbable polymer is selected from the group PLGA, PGA poly(glycolide), LPLA poly(l-lactide), DLPLA poly(dl-lactide), PCL poly(e-caprolactone) PDO, poly(dioxolane) PGA-TMC, 85/15 DLPLG p(dl-lactide-co-glycolide), 75/25 DLPL, 65/35 DLPLG, 50/50 DLPLG, TMC poly(trimethylcarbonate), p(CPP:SA) poly(1,3-bis-p-(carboxyphenoxy)propane-co-sebacic acid).

7. The composition of claim 1, wherein between 25% and 45% of the total amount of active agent in the composition is released after 24 hours in vitro release in a 1:1 spectroscopic grade ethanol/phosphate buffer saline at pH 7.4 and 37° C.; wherein the amount of the active agent released is determined by measuring UV absorption at 278 nm by a diode array spectrometer.

8. The composition of claim 1, wherein the composition is in a dosage form capable of being administered through a mode of administration selected from: (a) injection into the bladder to treat bladder cancer, (b) injection into the prostate gland to treat prostate cancer, (c) injection into or near the vitreous humor of the eye to treat ocular disease, and (d) injection into the nasal turbinates to treat chronic sinusitis.

9. The composition of claim 1, wherein the composition is in a dosage form capable of being injected into an intervention site wherein the intervention site is selected from: (a) the wall of a body cavity, (b) the wall of a body cavity resulting from partial or complete tumor removal, (c) a cannulized site within a subject, (d) a nasal turbinate, (e) within the reproductive system of a subject, (f) within the urinary system of a subject, (g) located at a tumor site, (f) a location in the ear, (g) a location in the esophagus, (h) a location in the larynx, (i) a location of an injury, (j) an infection site, (k) a surgery site, (l) an ocular site, (m) an inflammatory site, or (n) an arthritic joint.

10. The composition of claim 1, wherein the active agent and the polymer are in same layer, in separate layers, or form overlapping layers.

11. The composition of claim 1, the dosage form consisting essentially of the bioabsorbable polymer and the crystalline limus drug.

* * * * *